US009558551B2

(12) United States Patent
Motomura et al.

(10) Patent No.: US 9,558,551 B2
(45) Date of Patent: Jan. 31, 2017

(54) IMAGE MEASUREMENT APPARATUS AND IMAGE MEASUREMENT METHOD FOR DETERMINING A PROPORTION OF POSITIVE CELL NUCLEI AMONG CELL NUCLEI INCLUDED IN A PATHOLOGIC EXAMINATION SPECIMEN

(71) Applicant: Panasonic Corporation, Osaka (JP)

(72) Inventors: Hideto Motomura, Kyoto (JP); Yoshikuni Sato, Fukui (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 232 days.

(21) Appl. No.: 14/471,538

(22) Filed: Aug. 28, 2014

(65) Prior Publication Data

US 2014/0367555 A1  Dec. 18, 2014

Related U.S. Application Data

(63) Continuation of application No. PCT/JP2013/005990, filed on Oct. 8, 2013.

(30) Foreign Application Priority Data

Nov. 27, 2012  (JP) ................. 2012-258613

(51) Int. Cl.
*G06T 7/00* (2006.01)
*G02B 21/36* (2006.01)
(Continued)

(52) U.S. Cl.
CPC ......... *G06T 7/0012* (2013.01); *G01N 15/1475* (2013.01); *G02B 21/367* (2013.01);
(Continued)

(58) Field of Classification Search
CPC ................ G06T 7/0012; G06T 2207/10004; G06T 2207/10056; G06T 2207/10024; G06T 2207/30004
(Continued)

(56) References Cited

U.S. PATENT DOCUMENTS 6,348,325 B1  2/2002  Zahniser et al.
6,593,102 B2  7/2003  Zahniser et al.
(Continued)

FOREIGN PATENT DOCUMENTS

JP  2003-513270  4/2003
JP  2005-331394  12/2005
(Continued)

OTHER PUBLICATIONS

Yutaka Hatanaka et al., "Quantitative immunohistochemical evaluation of HER2/neu expression with HercepTest™ in breast carcinoma by image analysis", Pathology International, 2001.
(Continued)

*Primary Examiner* — Seung C Sohn
(74) *Attorney, Agent, or Firm* — Wenderoth, Lind & Ponack, L.L.P.

(57) ABSTRACT

An image measurement apparatus includes: a lighting unit that emits a first narrowband light with a bandwidth (i) narrower than a bandwidth of a visible light and (ii) including a dominant wavelength of a color of a positive cell nucleus; an image obtaining unit that obtains an examination image by capturing an image of a pathologic examination specimen to which the first narrowband light is emitted; a cell nuclei extracting unit that extracts pixels of positive cell nuclei from the examination image by comparing pixel values of the examination image with a predetermined threshold; a positive proportion calculating unit that calculates a proportion of the positive cell nuclei among cell (Continued)

nuclei included in the pathologic examination specimen, using the pixels of the positive cell nuclei extracted by the cell nuclei extracting unit; and an output unit that outputs the proportion.

9 Claims, 22 Drawing Sheets

(51) Int. Cl.
G06T 7/40 (2006.01)
G06T 7/60 (2006.01)
G01N 15/14 (2006.01)
G06K 9/00 (2006.01)
G01N 1/31 (2006.01)

(52) U.S. Cl.
CPC ........ G06K 9/00134 (2013.01); G06T 7/0014 (2013.01); G06T 7/408 (2013.01); G06T 7/602 (2013.01); G01N 1/312 (2013.01); G06T 2207/10004 (2013.01); G06T 2207/10024 (2013.01); G06T 2207/10056 (2013.01); G06T 2207/10152 (2013.01); G06T 2207/30004 (2013.01); G06T 2207/30024 (2013.01)

(58) Field of Classification Search
USPC ........................................ 250/208.1; 382/133
See application file for complete search history.

(56) References Cited

U.S. PATENT DOCUMENTS

| 6,661,501 B1 | 12/2003 | Zahniser et al. |
| 6,665,060 B1 | 12/2003 | Zahniser et al. |
| 7,006,674 B1 | 2/2006 | Zahniser et al. |
| 7,369,304 B2 | 5/2008 | Maenle et al. |
| 7,411,664 B2 | 8/2008 | Zahniser et al. |
| 7,446,935 B2 | 11/2008 | Maenle et al. |
| 7,468,836 B2 | 12/2008 | Maenle et al. |
| 7,538,861 B2 | 5/2009 | Zahniser et al. |
| 7,587,078 B2 | 9/2009 | Zahniser et al. |
| 7,667,890 B2 | 2/2010 | Maenle et al. |
| 7,826,648 B2 | 11/2010 | Arai |
| 2002/0150967 A1 | 10/2002 | Zahniser et al. |
| 2003/0179445 A1 | 9/2003 | Maenle et al. |
| 2004/0132197 A1 | 7/2004 | Zahniser et al. |
| 2006/0077538 A1 | 4/2006 | Zahniser et al. |
| 2006/0077541 A1 | 4/2006 | Zahniser et al. |
| 2006/0104499 A1 | 5/2006 | Zahniser et al. |
| 2006/0245630 A1 | 11/2006 | Zahniser et al. |
| 2007/0047804 A1 | 3/2007 | Arai |
| 2008/0013168 A1 | 1/2008 | Maenle et al. |
| 2008/0013812 A1 | 1/2008 | Maenle et al. |
| 2008/0018994 A1 | 1/2008 | Maenle et al. |
| 2008/0212866 A1 | 9/2008 | Lett et al. |
| 2008/0278707 A1 | 11/2008 | Zahniser et al. |
| 2009/0087074 A1* | 4/2009 | Wong ................. G06K 9/00147 382/133 |
| 2009/0245612 A1 | 10/2009 | Zahniser et al. |
| 2009/0269799 A1 | 10/2009 | Winkelman et al. |
| 2009/0317836 A1 | 12/2009 | Kuhn et al. |
| 2010/0054560 A1 | 3/2010 | Yamashita et al. |
| 2010/0111398 A1* | 5/2010 | Mitra ................... G06K 9/0014 382/133 |
| 2010/0128944 A1 | 5/2010 | Zahniser et al. |
| 2010/0284602 A1 | 11/2010 | Winkelman et al. |
| 2011/0014645 A1 | 1/2011 | Winkelman et al. |
| 2011/0070606 A1 | 3/2011 | Winkelman et al. |
| 2012/0021456 A1 | 1/2012 | Levine et al. |
| 2012/0262563 A1 | 10/2012 | Marcelpoil et al. |
| 2012/0327211 A1 | 12/2012 | Yamamoto |
| 2013/0070077 A1 | 3/2013 | Winkelman et al. |
| 2013/0094733 A1 | 4/2013 | Nosato et al. |
| 2014/0043461 A1 | 2/2014 | Otsuka |

FOREIGN PATENT DOCUMENTS

| JP | 2008-541048 | 11/2008 |
| JP | 2010-25758 | 2/2010 |
| JP | 2011-181015 | 9/2011 |
| JP | 2012-122852 | 6/2012 |
| JP | 2012-525592 | 10/2012 |
| JP | 2014-513292 | 5/2014 |
| WO | 01/33197 | 5/2001 |
| WO | 2006/118888 | 11/2006 |
| WO | 2008/108059 | 9/2008 |
| WO | 2010/126903 | 11/2010 |
| WO | 2012/011579 | 1/2012 |
| WO | 2012/142111 | 10/2012 |
| WO | 2012/147492 | 11/2012 |

OTHER PUBLICATIONS

Spiros Kostopoulos et al., "Colour-Texture based image analysis method for assessing the Hormone Receptors status in Breast tissue sections", Proceedings of the 29$^{th}$ Annual International Conference of the IEEE Embs, Cité Internationale, Lyon, France, Aug. 23-26, 2007, pp. 4985-4988.

International Search Report issued Dec. 10, 2013 in corresponding International Application No. PCT/JP2013/005990.

Extended European Search Report issued Nov. 4, 2015 in corresponding European Application No. 13857765.5.

Jozsef Bocsi et al., "Proliferation/apoptosis determination by tissue cytometry in gastrointestinal fresh frozen sections using triple labeling and automated scanning fluorescence microscopy", SPIE, Po Box 10, Bellingham, WA 98227-0010, USA, Jan. 1, 2006, XP040218595.

Varga, D. et al., "An automated scoring procedure for the micronucleus test by image analysis", Mutagenesis, IRL Press, Oxford, GB, vol. 19, No. 5, Jan. 1, 2004, pp. 391-397, XP002443946, ISSN: 0267-8357, DOI: 10.1093/MUTAGE/GEH047.

* cited by examiner

Light intensity

Wavelength (b)

Average 0.2   0.4   0.6

IMAGE MEASUREMENT APPARATUS AND IMAGE MEASUREMENT METHOD FOR DETERMINING A PROPORTION OF POSITIVE CELL NUCLEI AMONG CELL NUCLEI INCLUDED IN A PATHOLOGIC EXAMINATION SPECIMEN

CROSS REFERENCE TO RELATED APPLICATION

This is a continuation application of PCT Patent Application No. PCT/JP2013/005990 filed on Oct. 8, 2013, designating the United States of America, which is based on and claims priority of Japanese Patent Application No. 2012-258613 filed on Nov. 27, 2012. The entire disclosures of the above-identified applications, including the specifications, drawings and claims are incorporated herein by reference in their entirety.

FIELD

One or more exemplary embodiments disclosed herein relate generally to an image measurement apparatus and an image measurement method for supporting medical diagnosis or treatment.

BACKGROUND

Conventionally suggested is a technique that (i) identifies negative and positive cell nuclei through image processing, using color information of an image that is a captured image of pathological specimens and (ii) calculates a positive proportion indicating a proportion of positive cell nuclei among the total cell nuclei that is a sum of the negative and positive cell nuclei (for example, see PTL 1).

CITATION LIST

Patent Literature

[PTL 1] WO 2008/108059

SUMMARY

Technical Problem

The conventional technique cannot support color variation in the pathological specimens. The colors of pathological specimens are determined by various factors in preparing specimens, such as concentration of a fixative, a fixed time, a staining time, a room temperature, and humidity. Furthermore, different specimen preparation facilities use different reagents and devices. Thus, depending on each of the facilities, colors of pathological specimens vary. For this reason, the cell nuclei cannot be stably extracted, and the positive proportion cannot be accurately calculated.

One non-limiting and exemplary embodiment provides an image measurement apparatus and an image measurement method for (i) offsetting a color difference in an image of pathological specimens occurring due to a difference in preparing specimens, (ii) stably extracting a specific target, such as negative and positive cell nuclei, and (iii) thus enabling calculation of a positive proportion with high accuracy.

Solution to Problem

In one general aspect, the techniques disclosed here feature an image measurement apparatus including: a lighting unit configured to emit a first narrowband light that is a light with a bandwidth (i) narrower than a bandwidth of a visible light and (ii) including a dominant wavelength of a color of a positive cell nucleus; an image obtaining unit configured to obtain an examination image by capturing an image of a pathologic examination specimen to which the first narrowband light is emitted; a cell nuclei extracting unit configured to extract pixels of positive cell nuclei from the examination image by comparing pixel values of the examination image with a predetermined threshold; a positive proportion calculating unit configured to calculate a proportion of the positive cell nuclei among cell nuclei included in the pathologic examination specimen, using the pixels of the positive cell nuclei extracted by the cell nuclei extracting unit; and an output unit configured to output the proportion calculated by the positive proportion calculating unit.

With the configuration, the image of a pathologic examination specimen is captured in a state where the light in the narrow bandwidth including the dominant wavelength of colors of the positive cell nuclei is emitted to the pathologic examination specimen. Thus, the examination image has increased brightness in the positive cell nuclei. Conversely, when the dominant wavelength differs between positive cell nuclei and a tissue other than the positive cell nuclei, the tissue has decreased brightness. Thus, performing threshold processing on the examination image allows pixels of the positive cell nuclei to be extracted stably from the examination image. Accordingly, the positive proportion can be calculated with high accuracy.

These general or specific aspects may be implemented by a system, a method, an integrated circuit, a computer program, a computer-readable recording medium, such as a CD-ROM, or an arbitrary combination of the system, the method, the integrated circuit, the computer program, and the recording medium.

Advantageous Effects

The image measurement apparatus and method according to one or more exemplary embodiments or features disclosed herein stably extracts a specific target, such as negative and positive cell nuclei, and calculates a positive proportion with high accuracy.

BRIEF DESCRIPTION OF DRAWINGS

These and other objects, advantages and features of the invention will become apparent from the following description thereof taken in conjunction with the accompanying drawings that illustrate a specific embodiment of the present invention.

FIG. 8 illustrates an average of dominant wavelengths.

Figure 1:
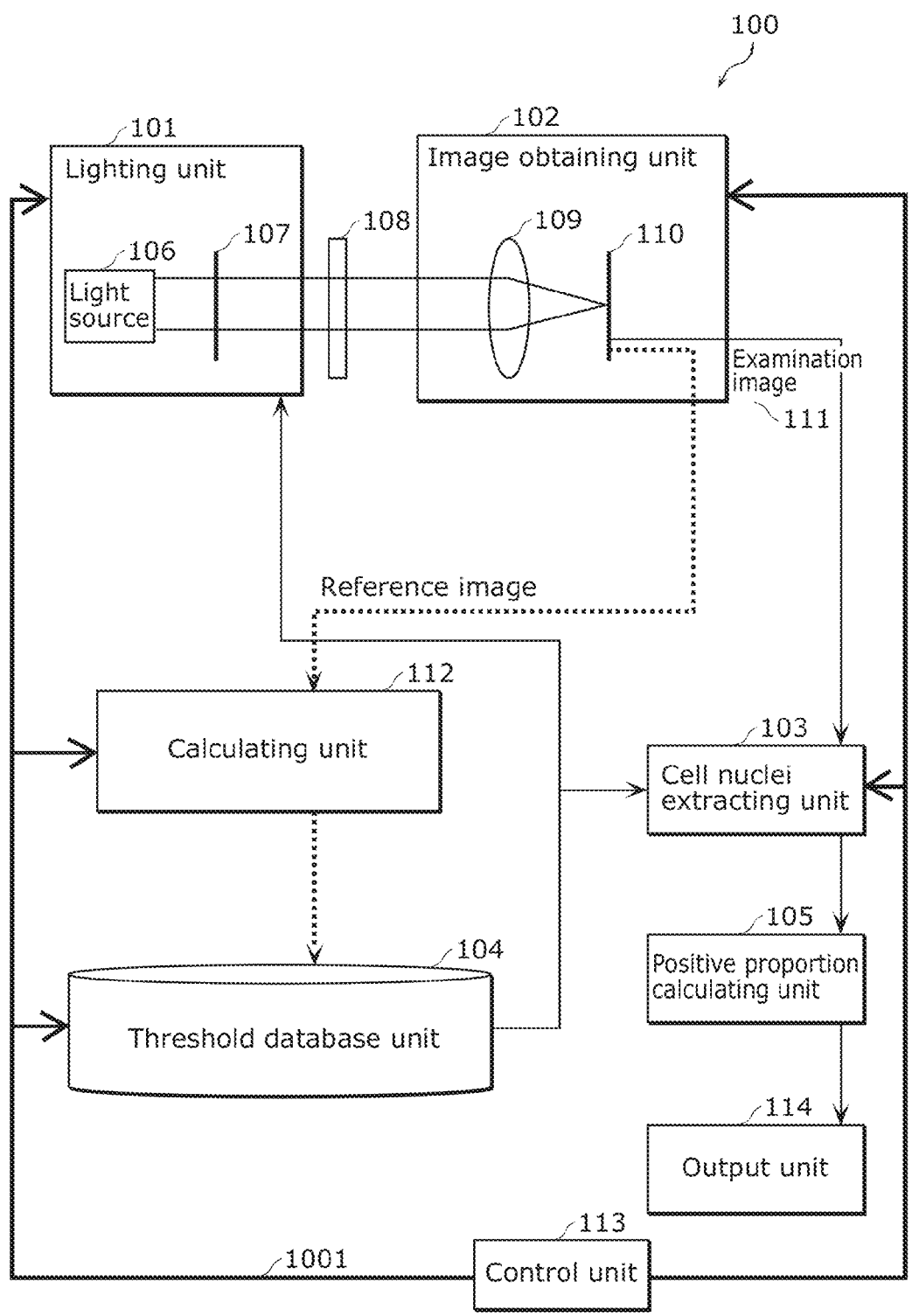
FIG. 1 is a block diagram illustrating a configuration of an image measurement apparatus according to Embodiment 1.

DESCRIPTION OF EMBODIMENTS (Underlying Knowledge Forming Basis of the Present Disclosure)

The diagnostics service has an objective of obtaining the name and state of a disease, and thus a treatment regimen is determined according to the name and the state of the disease. In order to determine the disease name or the disease state, pathological diagnostics is performed by taking a specimen from a lesion and observing the state on a cellular level. In the pathological diagnostics, the obtained specimen is sliced to a thickness that can be observed with a microscope to produce a sample. The image of the sample is captured with a digital camera or a scanner through the microscope, and the resulting digital image is stored and referenced.

Digitization of diagnostic images as described above greatly matches computerized data processing, and thus has provided more opportunities to assist physicians or technicians with their diagnostics service by using information technology (IT) systems. Computer-aided detection (CAD) is an example of such digitalization, and is a method of utilizing a computer in detection of a lesion.

For example, an effect of endocrine therapy for breast cancer can be determined by a percentage of the positive cell nuclei among the total number of cell nuclei (hereinafter referred to as "positive proportion"). The positive cell nuclei include positive estrogen receptor (ER) and positive progesterone receptor (PgR) that are extracted by staining cell nuclei. Here, the pathologists visually count the number of cell nuclei through observation using a microscope, and count the number of positive cell nuclei among them for calculating a positive proportion using the percentage of the positive cell nuclei to the total number of cell nuclei. However, the visual counting causes problems such as oversight and double counting, and has problems in reliability. The pathologists partially enlarge the image of pathological specimens using a microscope by moving a prepared slide, and normally observe pathological specimens in multiple parts. When a pathologist counts 500 cell nuclei from one view and takes four views, the number of counts reaches 2000. Thus, aside from the operation accuracy, the pathologist is burdened with the operation.

Here, PTL 1 discloses a technique of identifying negative and positive cell nuclei through image processing using color information of a pathological image, and calculating a positive proportion. In other words, blown positive cell nuclei and blue negative cell nuclei are counted, and the positive proportion is calculated from the count values. The blown positive cell nuclei and the blue negative cell nuclei are extracted using hue information, chroma information, and lightness information.

However, the conventional technique cannot support color variation in the pathological specimens. The color of a pathological specimen is determined by various factors in preparing specimens, such as concentration of a fixative, a fixed time, a staining time, a room temperature, and humidity. Furthermore, different specimen preparation facilities use different reagents and devices. Thus, depending on each of the facilities, the colors of pathological specimens vary.

When the negative and positive cell nuclei are extracted using color information, it is necessary to determine ranges of hue, chroma, and lightness for defining blown, and ranges of hue, chroma, and lightness for defining blue. However, once the color of a pathological specimen that is a target changes, the negative and positive cell nuclei cannot be stably extracted, and the positive proportion cannot be accurately calculated.

One non-limiting and exemplary embodiment provides the image measurement apparatus including: a lighting unit configured to emit a first narrowband light that is a light with a bandwidth (i) narrower than a bandwidth of a visible light and (ii) including a dominant wavelength of a color of a positive cell nucleus; an image obtaining unit configured to obtain an examination image by capturing an image of a pathologic examination specimen to which the first narrowband light is emitted; a cell nuclei extracting unit configured to extract pixels of positive cell nuclei from the examination image by comparing pixel values of the examination image with a predetermined threshold; a positive proportion calculating unit configured to calculate a proportion of the positive cell nuclei among cell nuclei included in the pathologic examination specimen, using the pixels of the positive cell nuclei extracted by the cell nuclei extracting unit; and an output unit configured to output the proportion calculated by the positive proportion calculating unit.

With the configuration, the image of the pathologic examination specimen is captured in a state where the narrowband light including the dominant wavelength of the color of the positive cell nucleus is emitted to the pathologic examination specimen. Thus, the examination image has increased brightness in the positive cell nuclei. Conversely, when the dominant wavelength differs between the positive cell nuclei and the other tissue, the tissue has decreased brightness. Thus, performing threshold processing on the examination image allows pixels of positive cell nuclei to be extracted stably from the examination image. Accordingly, the positive proportion can be calculated with high accuracy.

The lighting unit may be further configured to emit a broadband light that is a light with a bandwidth broader than the bandwidth of the first narrowband light, the image obtaining unit may be further configured to obtain a reference image by capturing an image of a pathologic examination specimen to which the broadband light is emitted, and the image measurement apparatus may further include: a dominant wavelength calculating unit configured to calculate a dominant wavelength of a color of a positive cell nucleus included in the reference image; and a threshold calculating unit configured to calculate, as the predetermined threshold, a threshold for extracting pixels of positive cell nuclei from the reference image by performing threshold processing, based on a light intensity of the dominant wavelength calculated by the dominant wavelength calculating unit.

It is possible to calculate, using a color, a dominant wavelength of light corresponding to the color. According to this method, it is possible to accurately calculate a dominant wavelength of a color of a positive cell nucleus. In other words, when light is emitted to tissue, the dominant wavelength of light with which the brighter image of the positive cell nucleus is captured can be calculated. Thus, a threshold for extracting pixels of the positive cell nuclei can be accurately calculated through threshold processing.

Furthermore, the dominant wavelength calculating unit may be configured to calculate a dominant wavelength of each of colors of the positive cell nuclei included in the reference image, the colors of the positive cell nuclei including the color of the positive cell nucleus, the image measurement apparatus may further comprise a distribution center calculating unit configured to calculate a center wavelength of the dominant wavelengths of the colors of the positive cell nuclei calculated by the dominant wavelength calculating unit, and the lighting unit may be configured to emit, as the first narrowband light, a light with a bandwidth (i) narrower than the bandwidth of the visible light and (ii) including the center wavelength calculated by the distribution center calculating unit.

With the configuration, a threshold can be calculated after offsetting the variation of dominant wavelengths occurring from the variation in colors of positive cell nuclei.

The dominant wavelength calculating unit may be further configured to calculate a complementary dominant wavelength of colors of the positive cell nuclei included in the reference image when the colors do not have any dominant wavelength, the threshold calculating unit may be configured to calculate, as the predetermined threshold, a threshold for extracting pixels of the positive cell nuclei from the reference image by performing the threshold processing, based on a light intensity of the complementary dominant wavelength calculated by the dominant wavelength calculating unit, the lighting unit may be configured to emit, in place of the first narrowband light, a second narrowband light that is a light with a bandwidth (i) narrower than the bandwidth of the visible light and (ii) including the complementary dominant wavelength, and the image obtaining unit may be further configured to obtain an examination image by capturing an image of a pathologic examination specimen to which the second narrowband light is emitted.

Depending on some color, a dominant wavelength of light corresponding to the color may not be calculated. In such a case, a complementary dominant wavelength can be calculated. In an examination image captured in a state where a narrowband light including the complementary dominant wavelength is emitted to the pathologic examination specimen, the positive cell nuclei have decreased brightness. Thus, when the image of the positive cell nuclei is less bright than other tissue in the examination image, a threshold for extracting pixels of the positive cell nuclei by performing threshold processing can be accurately calculated.

Furthermore, the lighting unit may be configured to emit, in place of the first narrowband light, a third narrowband light that is a light with a bandwidth (i) narrower than the bandwidth of the visible light and (ii) including a dominant wavelength of a color of a tissue other than the positive cell nuclei, and the image obtaining unit may be further configured to obtain an examination image by capturing an image of a pathologic examination specimen to which the third narrowband light is emitted.

The tissue other than the positive cell nuclei sometimes has brightness as much as the positive cell nuclei in the examination image when the narrowband light including the dominant wavelength of the color of the positive cell nucleus is emitted to the pathologic examination specimen. In such a case, emission of the third narrowband light including the dominant wavelength of the tissue to the pathologic examination specimen results in decreased brightness in the image of the positive cell nuclei and increased brightness in the image of the tissue. Thus, pixels of the positive cell nuclei can be accurately extracted through the threshold processing.

The dominant wavelength calculating unit may be further configured to calculate the dominant wavelength of the color of the tissue included in the reference image, and the threshold calculating unit may be further configured to calculate, as the predetermined threshold, a threshold for extracting the pixels of the positive cell nuclei from the reference image by performing the threshold processing, based on a light intensity of the dominant wavelength of the color of the tissue calculated by the dominant wavelength calculating unit.

With the configuration, a threshold for extracting pixels of the positive cell nuclei from the examination image captured with the third narrowband light emitted can be accurately calculated.

The image measurement apparatus may further comprise a control unit configured to move an imaging surface of the image obtaining unit to a position on which the first narrowband light is focused, the first narrowband light being emitted by the lighting unit.

With the effect of chromatic aberration in an imaging optical system, the focus point of light entering the imaging optical system differs for each light wavelength. With the configuration, since an imaging surface is moved according to a wavelength of light emitted to the pathologic examination specimen, a focused examination image can be obtained.

Furthermore, the bandwidth of the first narrowband light may be smaller than a bandwidth of a light that passes through one of RGB color filters.

These general or specific aspects may be implemented by a system, a method, an integrated circuit, a computer program, a computer-readable recording medium, such as a CD-ROM, or an arbitrary combination of the system, the method, the integrated circuit, the computer program, and the recording medium.

Embodiments will be described in detail with reference to the drawings.

Embodiments to be described below are all general or specific examples. The values, shapes, materials, constituent elements, positions and connections of the constituent elements, steps, and orders of the steps indicated in Embodiments are examples, and do not limit the scope of the appended Claims and their equivalents. The constituent elements in Embodiments that are not described in independent Claims that describe the most generic concept are described as arbitrary constituent elements.

Embodiment 1

Embodiment 1 describes an image measurement apparatus that can calculate a positive proportion using a fixed threshold database by obtaining data of dominant wavelengths of negative and positive cell nuclei included in a pathological specimen prepared from a specimen of a lesion, irrespective of color differences caused by differences in preparing specimens.

FIG. 1 is a block diagram illustrating a configuration of an image measurement apparatus according to Embodiment 1.

An image measurement apparatus 100 includes a lighting unit 101, an image obtaining unit 102, a cell nuclei extracting unit 103, a threshold database unit 104, a positive proportion calculating unit 105, a calculating unit 112, a control unit 113, and an output unit 114. The image measurement apparatus 100 detects a positive proportion given from a pathologic examination specimen 108. The pathologic examination specimen 108 is prepared by slicing a specimen submitted from a lesion of a human body and others, to a thickness that can be observed with, for example, a microscope.

The lighting unit 101 includes a light source 106 and a narrowband light conversion unit 107. The narrowband light conversion unit 107 transmits light with a partial bandwidth of light given from the light source 106 that outputs light covering the entire visible light bandwidth, and produces light close to monochromatic light. The light of the lighting unit 101 is emitted to the pathologic examination specimen 108, and reaches the image obtaining unit 102.

Figure 2A:
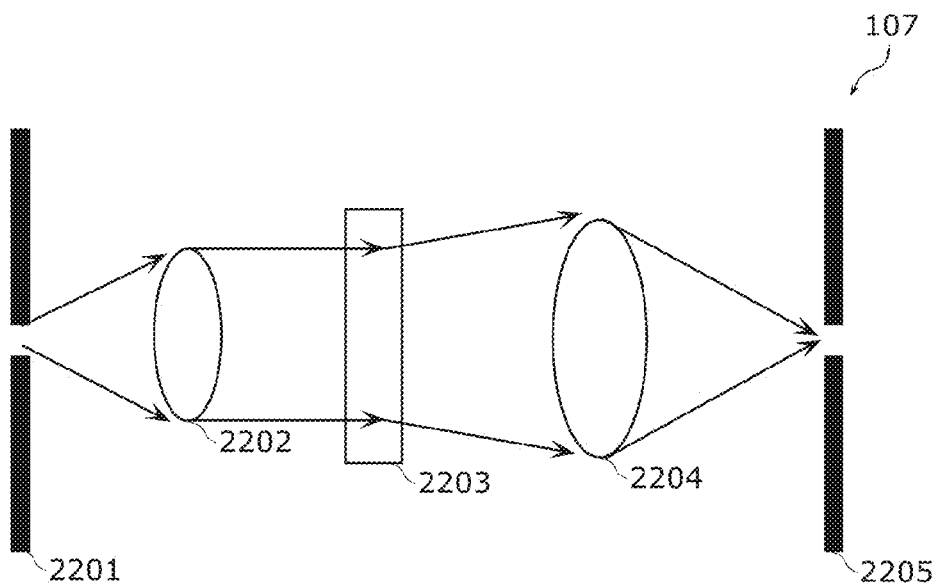
FIG. 2A illustrates a detailed configuration of a narrowband light conversion unit.

FIG. 2A illustrates a detailed configuration of the narrowband light conversion unit 107. The narrowband light conversion unit 107 includes a slit 2201, a collimate lens 2202, a grating 2203, a focus lens 2204, and a slit 2205.

The slit 2201 is an opening that introduces light of the light source 106.

The collimate lens 2202 converts light from the slit 2201 to parallel light.

The grating 2203 disperses light from the collimate lens 2202 at a different diffraction angle for each wavelength. The grating 2203 disperses light according to a diffraction grating equation indicated in Math 1 below.

[Math 1]

$$d(\sin \alpha \pm \sin \beta) = m\lambda \quad \text{(Equation 1)}$$

Figure 2B:
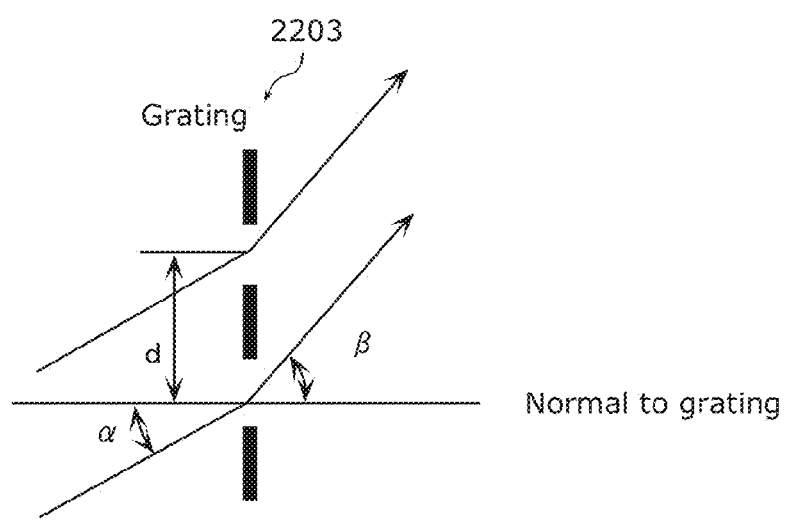
FIG. 2B illustrates spacing of gratings, incident angles, and diffraction angles.

Here, d denotes a spacing of gratings, α denotes an incident angle, β denotes a diffraction angle, m denotes a diffraction order (0, ±1, ±2, ... ), and λ denotes a wavelength. FIG. 2B illustrates each of the relationships.

A focus lens 2204 forms images of the light dispersed by the grating 2203 on the slit 2205 in wavelength order.

The slit 2205 only transmits light at necessary wavelengths. Accordingly, the light at a narrow bandwidth from the lighting unit 101 can be transmitted.

Figure 3:
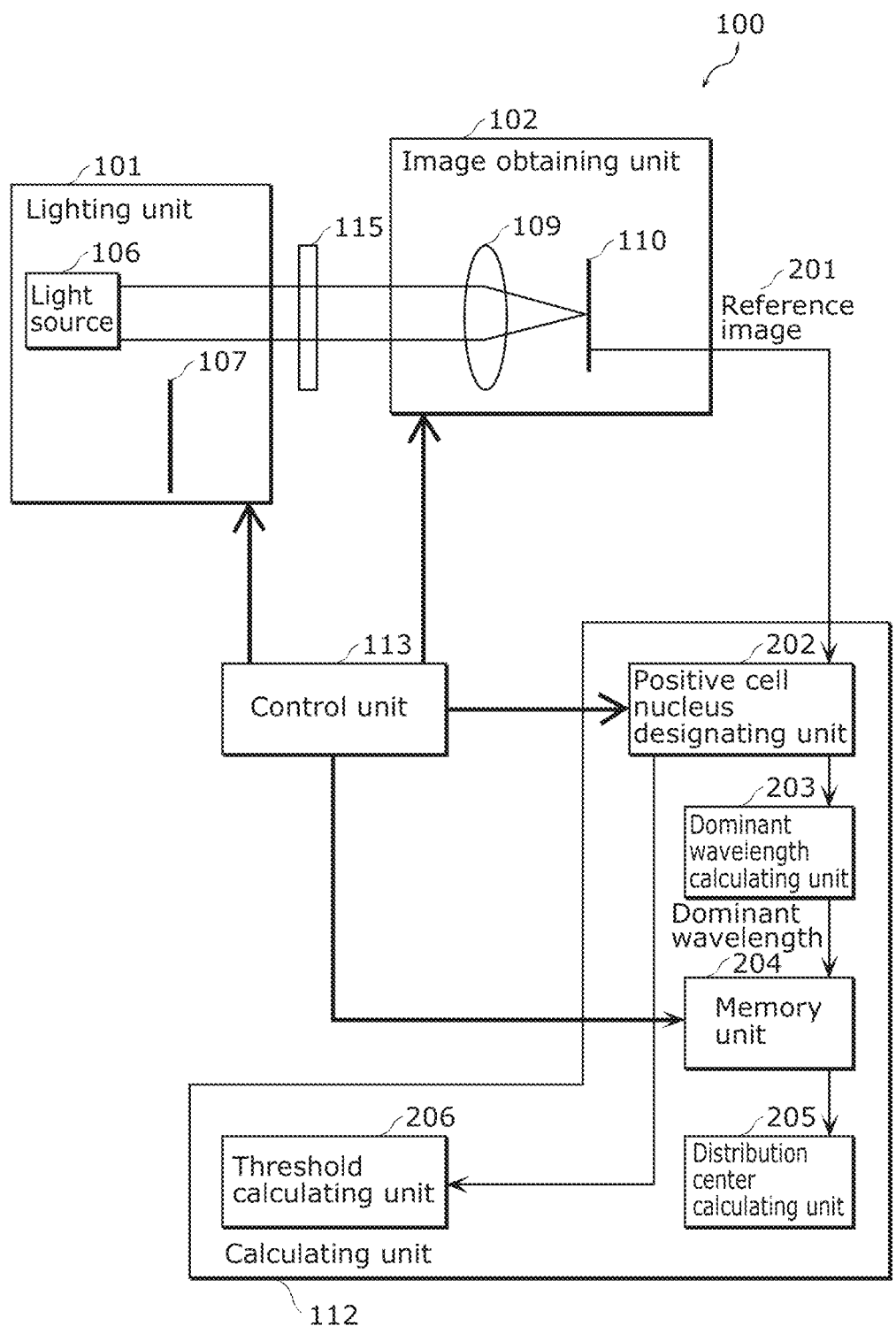
FIG. 3 illustrates a method of calculating a dominant wavelength of positive cell nuclei by an image measurement apparatus in the preparation mode.

As illustrated in FIG. 3, the lighting unit 101 can also output the light covering the entire visible light bandwidth when the narrowband light conversion unit 107 is excluded from the light path. Here, the light that passes through the narrowband light conversion unit 107 will be referred to as "narrowband light", and the light emitted from the light source 106 in a state where the narrowband light conversion unit 107 is excluded from the light path will be referred to as "broadband light".

Generally, imagers use red (R), green (G), and blue (B) for color separation. The visible light bandwidth approximately ranges from 400 to 700 nm with a width of 300 nm. Thus, the bandwidth of light that has passed from each of RGB color filters has approximately a half width of 100 nm. The narrow bandwidth according to Embodiment 1 indicates a half width narrower than those of general RGB color filters, that is, approximately a half width smaller than 100 nm. Preferably, the narrow bandwidth according to Embodiment 1 ranges from 30 to 70 nm.

When the light source 106 has several light source elements that can emit light with a narrow bandwidth, it can emit light with a narrow bandwidth without the narrowband light conversion unit 107. The internal configuration of the lighting unit 101 illustrated in FIG. 1 is one example. As long as the lighting unit 101 is a lighting fixture that can output both of narrowband light and broadband light, it does not limit the scope of the appended Claims and their equivalents.

The image obtaining unit 102 includes an imaging optical system 109 and an imaging sensor 110. The imaging optical system 109 causes the imaging sensor 110 to provide an image using light from the lighting unit 101. The imaging sensor 110 captures an image of the pathologic examination specimen 108 to obtain a concentration distribution of the pathologic examination specimen 108, and outputs the concentration distribution as an examination image 111.

The cell nuclei extracting unit 103 extracts positive cell nuclei from the examination image 111 by performing threshold processing on the examination image 111 using a positive cell nuclei extraction threshold stored in the threshold database unit 104.

The calculating unit 112 calculates a threshold for extracting the positive cell nuclei (hereinafter referred to as "positive cell nuclei extraction threshold") that is to be stored in the threshold database unit 104, in advance before calculating the positive proportion. Thus, the image measurement apparatus 100 stores the positive cell nuclei extraction threshold in the threshold database unit 104 as advance preparation before calculating the positive proportion. The calculation of a positive proportion will be referred to as "execution mode", and the calculation of a positive cell nuclei extraction threshold will be referred to as "preparation mode" in the following description.

The control unit 113 controls operations of the image measurement apparatus 100 in the execution mode and the preparation mode. Furthermore, in FIG. 1, broken lines indicate data flow only in the preparation mode.

Figure 4:
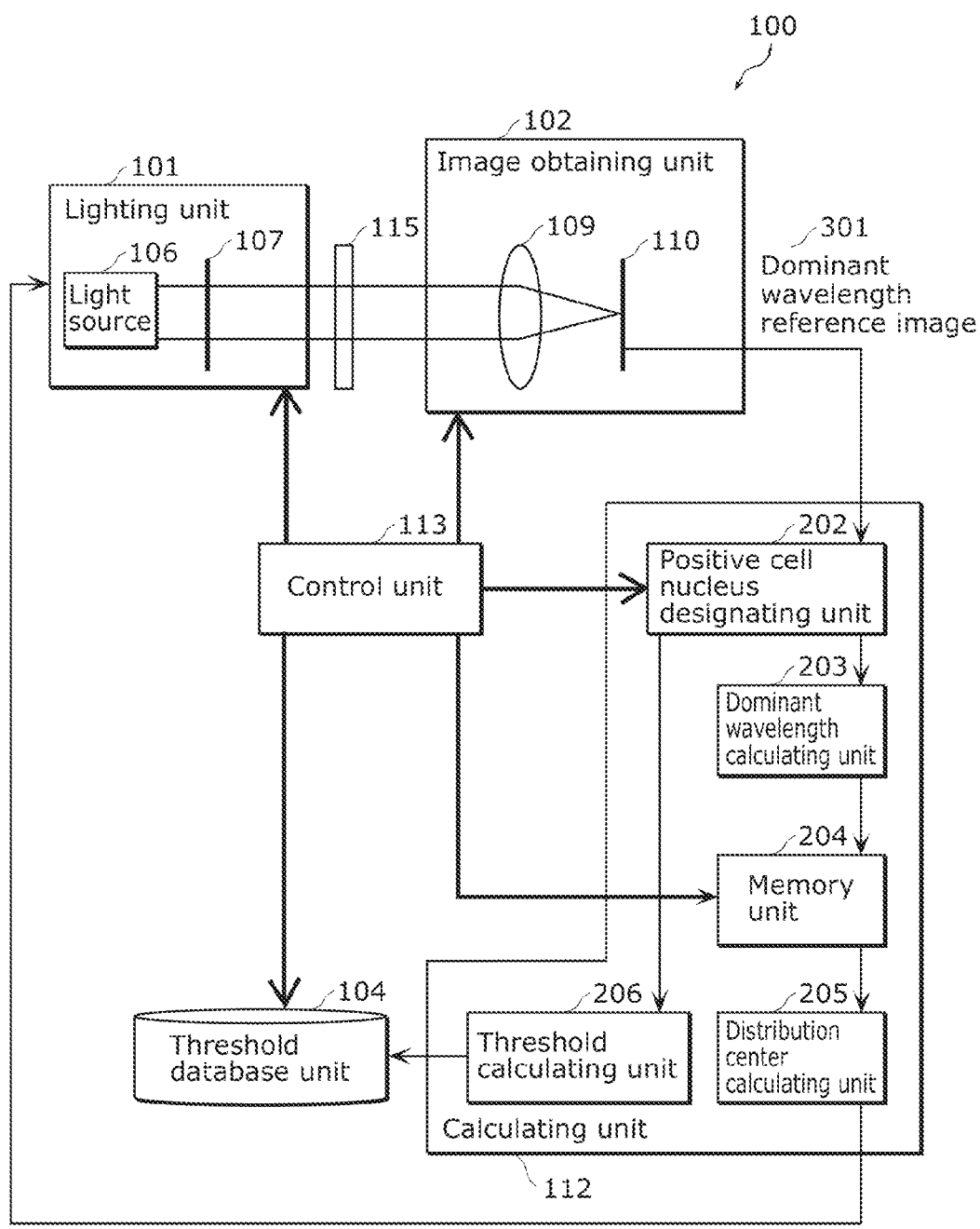
FIG. 4 illustrates processing by the image measurement apparatus in the preparation mode for emitting a narrowband light including the dominant wavelength of the positive cell nuclei to a pathologic reference specimen and calculating a positive cell nuclei extraction threshold.

In the preparation mode, the calculating unit 112 calculates a positive cell nuclei extraction threshold, and stores it in the threshold database unit 104. The calculation consists of calculating a dominant wavelength of colors of the positive cell nuclei and obtaining pixel values of the positive cell nuclei. As illustrated in FIG. 3, the former operation is performed in a state where the narrowband light conversion unit 107 is excluded from the light path and light is emitted from the light source 106 to a pathologic reference specimen 115. As illustrated in FIG. 4, the latter operation is performed in a state where the light that has passed from the light source 106 through the narrowband light conversion unit 107 is emitted to the pathologic reference specimen 115. Here, the pathologic reference specimen 115 is a specimen prepared by the same processing as that of the pathologic examination specimen 108, and thus may be the same as the pathologic examination specimen 108.

Figure 5:
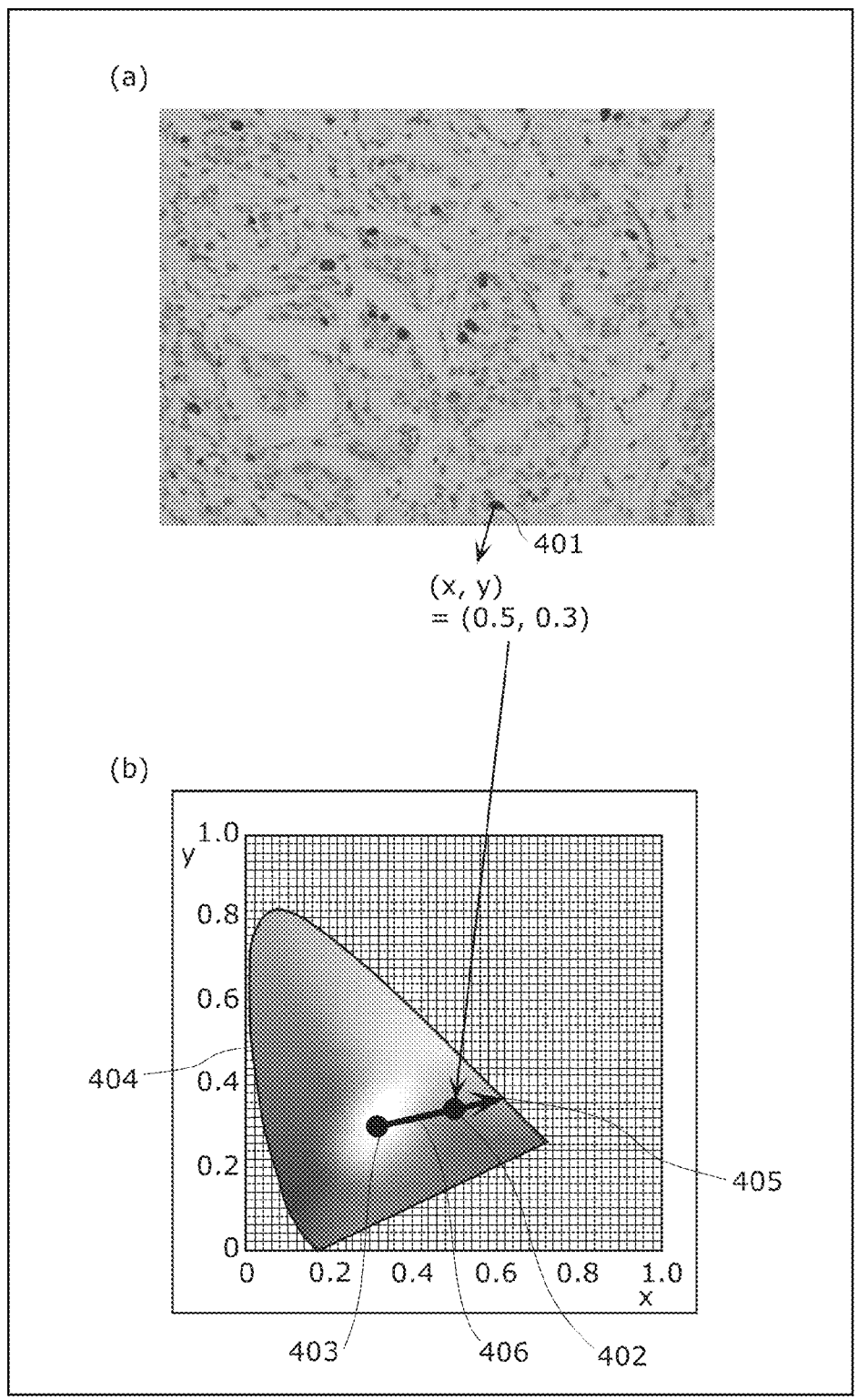
FIG. 5 illustrates a dominant wavelength of a color of positive cell nuclei.
Figure 6:
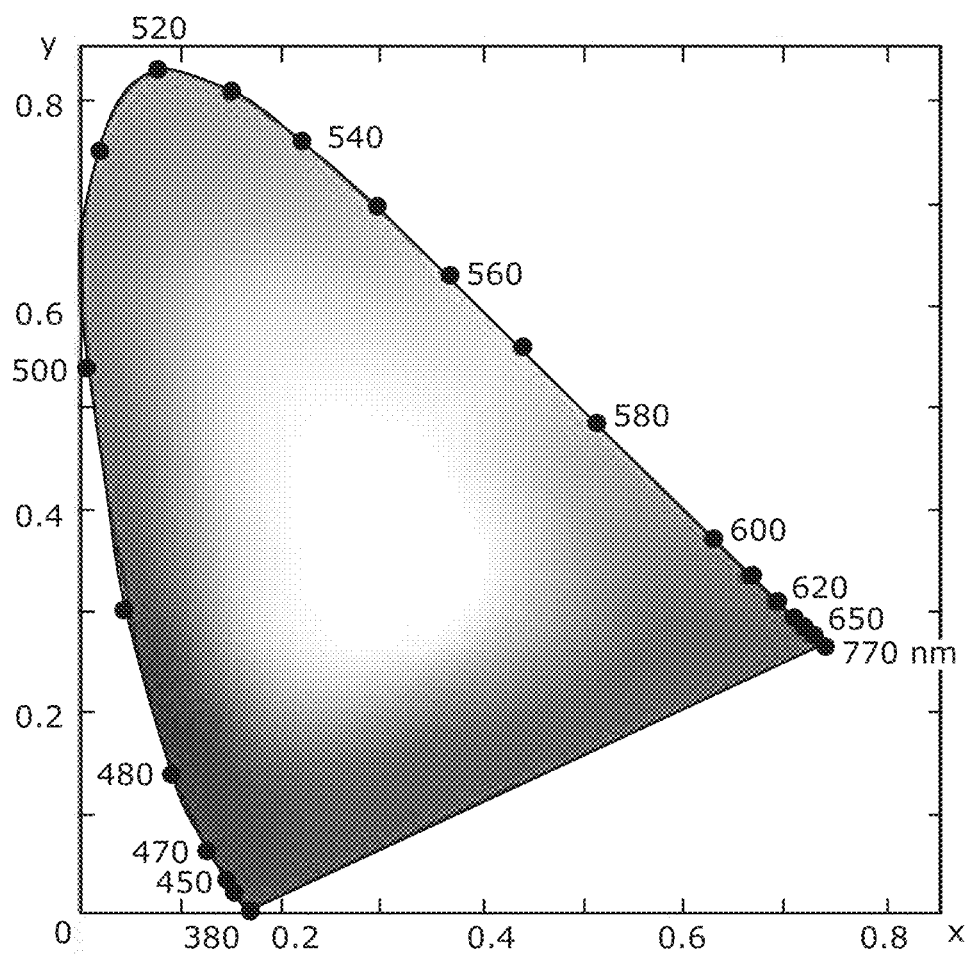
FIG. 6 indicates a distribution of a dominant wavelength in an x-y chromaticity diagram.
Figure 7:
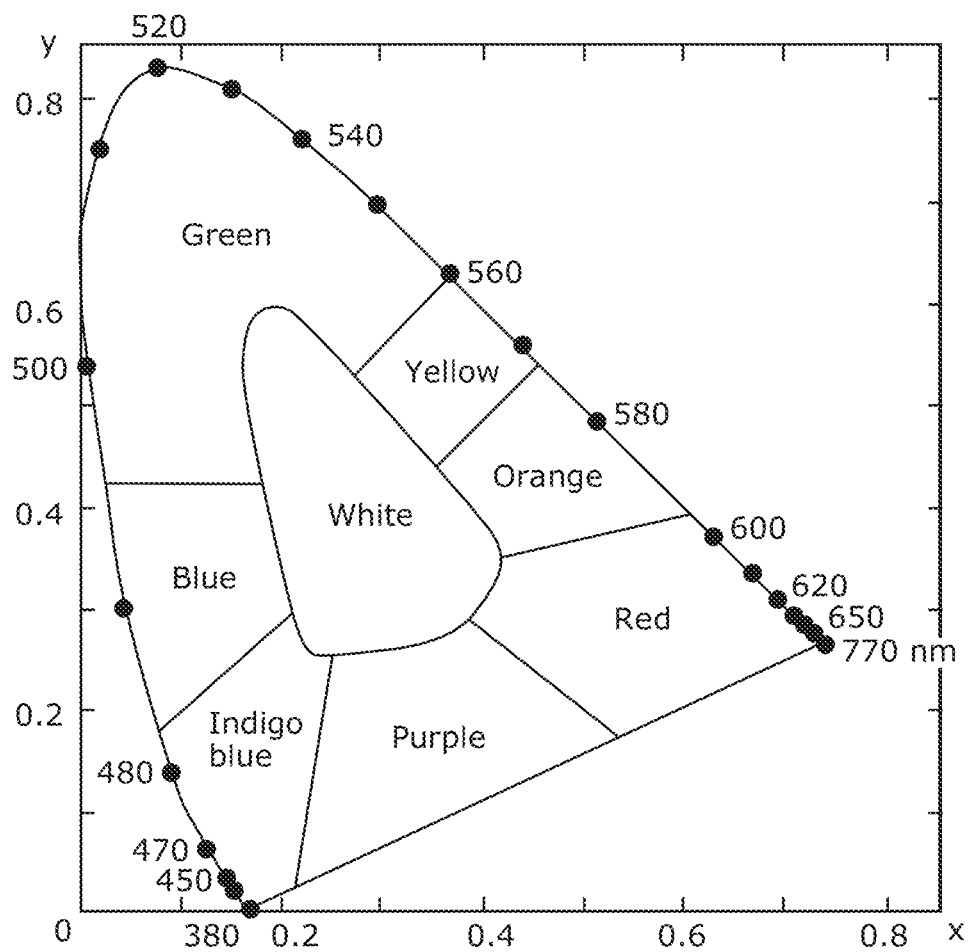
FIG. 7 indicates rough color segmentation in an x-y chromaticity diagram.

When a color is created by a mixture of white light and monochromatic light, the dominant wavelength indicates a wavelength of the monochromatic light. For example, suppose that the color of a positive cell nucleus 401 illustrated in (a) of FIG. 5 is indicated by coordinates (x, y)=(0.5, 0.3) in an x-y chromaticity diagram of (b) of FIG. 5. The color of a point 402 (x, y)=(0.5, 0.3) can be created by a mixture of the white light indicated by a white point 403 and the monochromatic light indicated by a point 405 on a spectral locus 404. FIG. 6 indicates a distribution of dominant wavelengths in the x-y chromaticity diagram. The dominant wavelengths are numerically indicated along with the spectral locus. The example of (b) of FIG. 5 shows that the dominant wavelength is approximately 600 nm. The dominant wavelength represents a hue using a wavelength of monochromatic light. The wavelength of 600 nm roughly shows a color in the red range. Although a spectral distribution cannot be calculated using a chromaticity value, the peak wavelength of the spectral distribution can be approximately estimated by calculating the dominant wavelength. FIG. 7 indicates rough color segmentation in an x-y chromaticity diagram. The central portion is categorized as a white area. Around the white area, areas each of which corresponds to red, orange, yellow, green, blue, indigo blue, and purple exist.

The segmentation can be used for suppressing influence of variation in colors of a pathological specimen. In other words, the color variation is equivalent to change in chromaticity value. Slight change in spectral distribution also changes a chromaticity value. However, change in chroma of a color does not change the dominant wavelength. Similarly, the chroma corresponding to a distance from the white point 403 in the x-y chromaticity diagram does not change the dominant wavelength. Furthermore, since lightness is unrelated to color shade, change in the lightness does not change the dominant wavelength.

Here, chromaticity of pixels belonging to positive cell nuclei is calculated using a pathological image that is a captured image of a pathological specimen. Then, the dominant wavelength is calculated using a point of intersection (white point 405) of (i) a line 406 connecting the point 402 to the white point 403 and (ii) the spectral locus 404. Calculating dominant wavelengths of all pixels belonging to positive cell nuclei for each pathological image and obtaining an average of the dominant wavelengths results in a dominant wavelength robust in color variation. (a) of FIG. 8 is a graph indicating a spectral distribution for each of positive cell nuclei. (b) of FIG. 8 indicates a line corresponding to the line 406 for each of the positive cell nuclei, and an average of the lines. The point of intersection of the average of the lines and the spectral locus corresponds to an average value of the dominant wavelengths.

In order to calculate a dominant wavelength of positive cell nuclei, (i) the control unit 113 sets the image measurement apparatus 100 to the preparation mode, and (ii) the lighting unit 101 emits light covering the entire visible light bandwidth to the pathologic reference specimen 115 with the narrowband light conversion unit 107 excluded from the light path as illustrated in FIG. 3. Thus, the imaging sensor 110 outputs a reference image 201 colored as the pathologic reference specimen 115.

The calculating unit 112 includes a positive cell nucleus designating unit 202, a dominant wavelength calculating unit 203, a memory unit 204, a distribution center calculating unit 205, and a threshold calculating unit 206.

Figure 9:
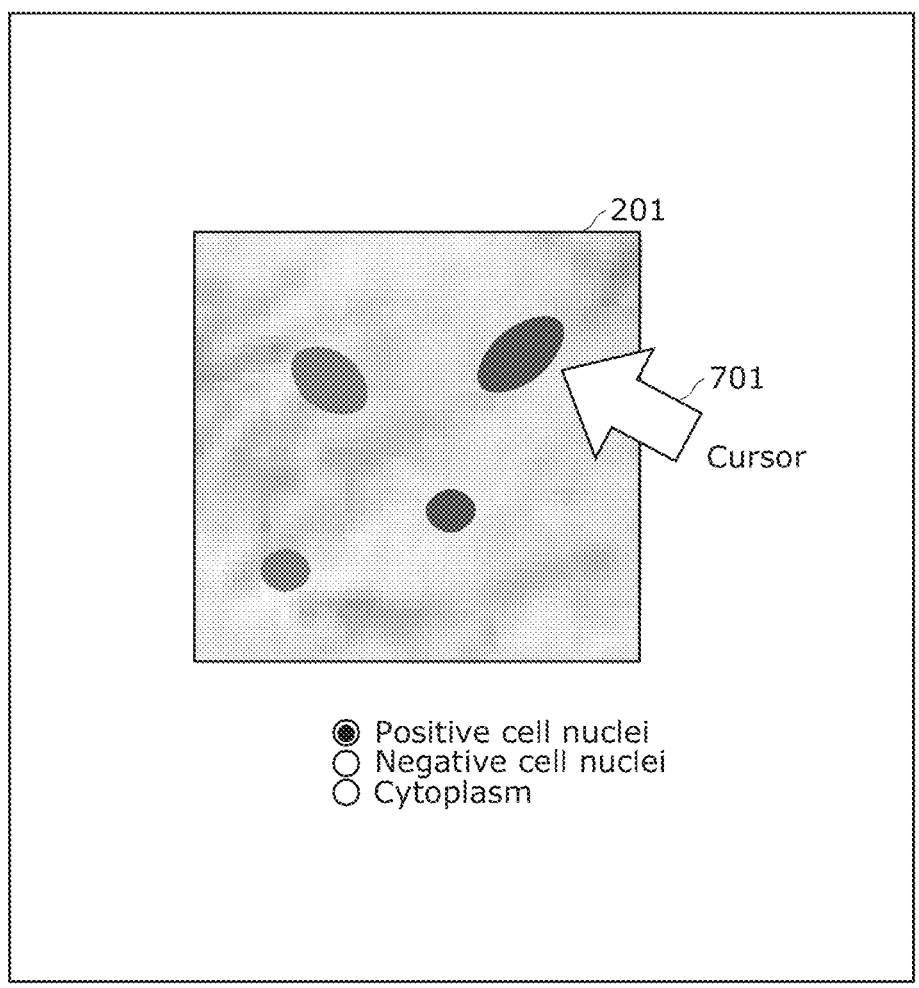
FIG. 9 illustrates a method for designating types of tissue and positions of the tissue.

The positive cell nucleus designating unit 202 designates positions of positive cell nuclei included in the reference image 201. The designating method is arbitrary. For example, the positive cell nucleus designating unit 202 may cause an operator of the image measurement apparatus 100 to designate a position of the positive cell nucleus. As illustrated in FIG. 9, the operator of the image measurement apparatus 100 selects the name of tissue (herein, positive cell nuclei) using, for example, a mouse in a state where the reference image 201 is displayed on a display connected to the image measurement apparatus 100. Then, the operator may move a cursor 701 on the positive cell nuclei included in the reference image 201 to designate the position of the positive cell nucleus. As will be described later, information on the position of the positive cell nucleus designated by the positive cell nucleus designating unit 202 is output to the dominant wavelength calculating unit 203 and the threshold calculating unit 206. The control unit 113 controls the positive cell nucleus designating unit 202.

The dominant wavelength calculating unit 203 calculates the dominant wavelength for each of the pixels designated as belonging to the positive cell nuclei. In other words, the dominant wavelength calculating unit 203 converts the pixel values (R, G, B) of the reference image into tristimulus values (X, Y, Z) in accordance with the following Equation 2.

[Math 2]

$$\begin{bmatrix} X \\ Y \\ Z \end{bmatrix} = \begin{bmatrix} 0.45 & 0.32 & 0.18 \\ 0.24 & 0.67 & 0.09 \\ 0.03 & 0.14 & 0.92 \end{bmatrix} \begin{bmatrix} R \\ G \\ B \end{bmatrix}$$ (Equation 2)

Here, the pixel values (R, G, B) indicate luminance linear signals. The 3×3 conversion factors of Equation 2 are examples, and one or more exemplary embodiments disclosed herein do not limit the factors.

The dominant wavelength calculating unit 203 converts the tristimulus values (X, Y, Z) into chromaticity coordinates (x, y) in accordance with the following Equation 3.

[Math 3]

$$x = \frac{X}{X+Y+Z}$$
$$y = \frac{Y}{X+Y+Z}$$ (Equation 3)

The dominant wavelength calculating unit 203 calculates the line 406 by connecting the white point 403 that is predetermined to the points on the x and y coordinates that are calculated in accordance with Equation 3. The dominant wavelength calculating unit 203 calculates the point of intersection of the line 406 and the spectral locus 404, and determines the dominant wavelength corresponding to the point of intersection with reference to the distribution of the dominant wavelength indicated in FIG. 6.

The memory unit 204 stores a dominant wavelength data item for each of the pixels of the positive cell nuclei in the reference images.

The distribution center calculating unit 205 reads the dominant wavelength data item from the memory unit 204 in accordance with an instruction from the control unit 113. The distribution center calculating unit 205 calculates a wavelength corresponding to the distribution center, using the dominant wavelength data items stored in the memory unit 204. The method of calculating the distribution center is arbitrary. For example, the distribution center calculating unit 205 calculates an arithmetic mean or a median of the dominant wavelengths as a distribution center.

FIG. 4 illustrates processing for calculating a positive cell nuclei extraction threshold with emission of the narrowband light including the dominant wavelength of the positive cell nuclei to the pathologic reference specimen 115.

The lighting unit 101 obtains the dominant wavelength from the distribution center calculating unit 205, and emits to the pathologic examination specimen 115 the narrowband light in which the obtained dominant wavelength is the center wavelength. The lighting unit 101 emits the narrowband light to the pathologic examination specimen 115 by transmitting light with the obtained dominant wavelength using the narrowband light conversion unit 107 as, for example, a grating.

Figure 10:
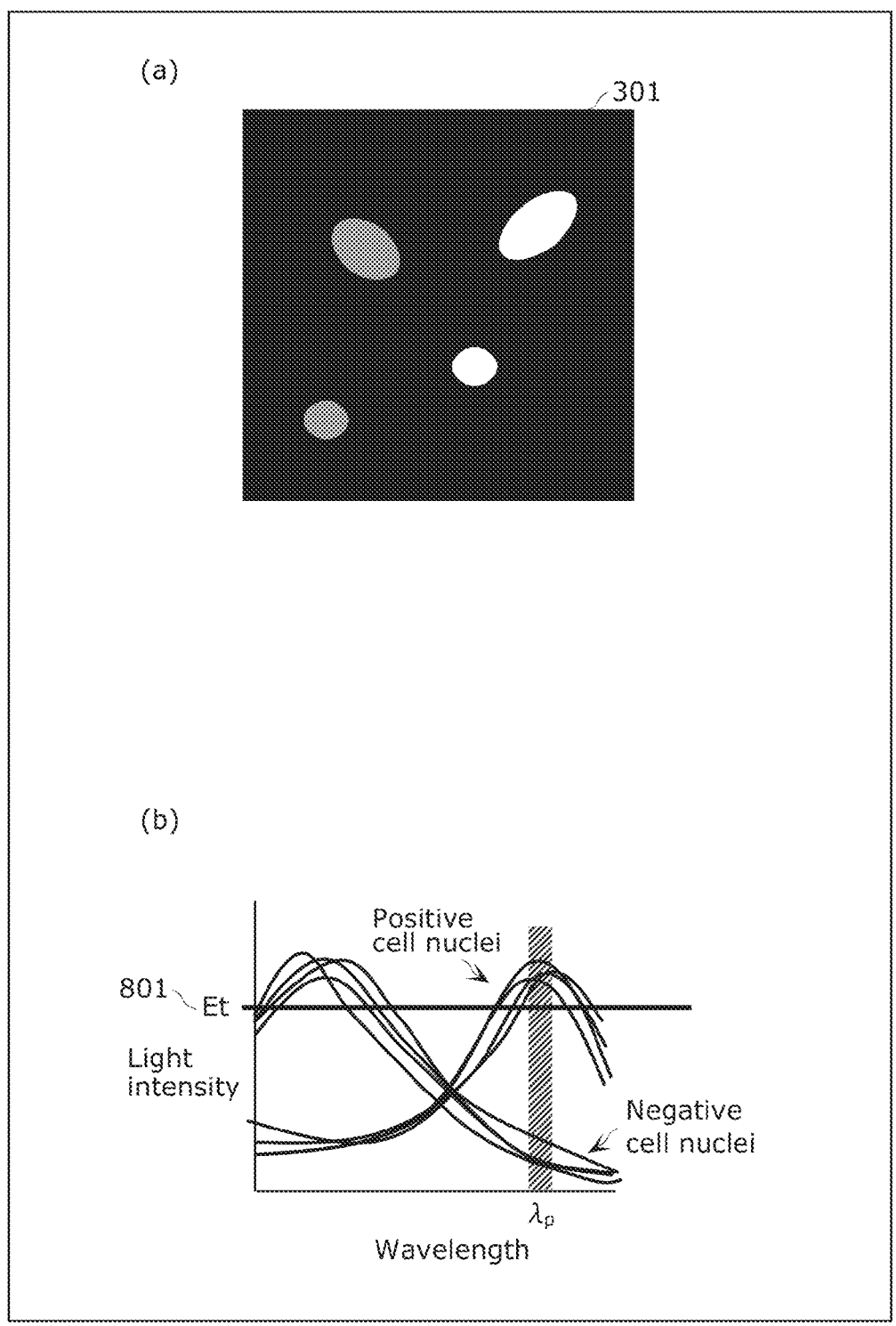
FIG. 10 illustrates setting of a threshold for extracting positive cell nuclei.

The image obtaining unit 102 obtains a dominant wavelength reference image 301 by capturing an image of the pathologic examination specimen 115 to which the narrowband light is emitted. (a) of FIG. 10 illustrates an example of the dominant wavelength reference image 301. The dominant wavelength reference image 301 is a monochrome image. In other words, only the narrowband light including the dominant wavelength $\lambda_p$ enters the imaging sensor 110. Thus, only one of the RGB sensors receives the major light. Thus, the input signal for the color sensor distant from the dominant wavelength is very low. Accordingly, the dominant wavelength reference image 301 does not have to be described in RGB. Here, the imaging sensor 110 converts the dominant wavelength reference image 301 in RGB into a luminance signal Y in accordance with the following Equation 4.

$$Y=0.24R+0.67G+0.09B \qquad \text{(Equation 4)}$$

One or more exemplary embodiments disclosed herein do not limit whether the dominant wavelength reference image 301 is described in RGB or Y, and the use of Y is a mere example. The coefficients in Equation 4 for calculating the luminance are examples, and the embodiments do not limit the coefficients.

Figure 11:
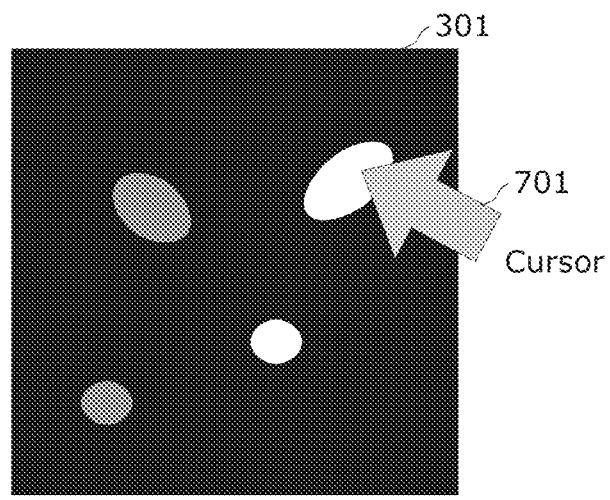
FIG. 11 illustrates a method of designating a positive cell nucleus in a dominant wavelength reference image.

The positive cell nucleus designating unit 202 designates the position of the positive cell nucleus included in the dominant wavelength reference image 301 by performing the same processing as described above. In other words, the positive cell nucleus designating unit 202 designates the position of the positive cell nucleus included in the dominant wavelength reference image 301 by an operator using the cursor 701 as illustrated in FIG. 11. The positive cell nucleus designating unit 202 outputs the position of the designated positive cell nucleus (coordinates of the pixel belonging to the positive cell nucleus), to the threshold calculating unit 206 in accordance with the control unit 113.

The threshold calculating unit 206 checks the distribution of the pixel values of the positive cell nuclei in the dominant wavelength reference image 301, and calculates the threshold for extracting the positive cell nuclei. For example, when the wavelengths of light corresponding to the negative and positive cell nuclei as indicated in (b) of FIG. 10 are distributed and the pixel value of the dominant wavelength $\lambda_p$ of the positive cell nuclei is larger than the pixel value corresponding to a light intensity Et801, the pixel can be determined as that of the positive cell nucleus. The threshold calculating unit 206 calculates the pixel value corresponding to the light intensity Et801 from the distribution of the pixel values of the positive cell nuclei, and stores the calculated pixel value as a positive cell nuclei extraction threshold in the threshold database unit 104.

Figure 12:
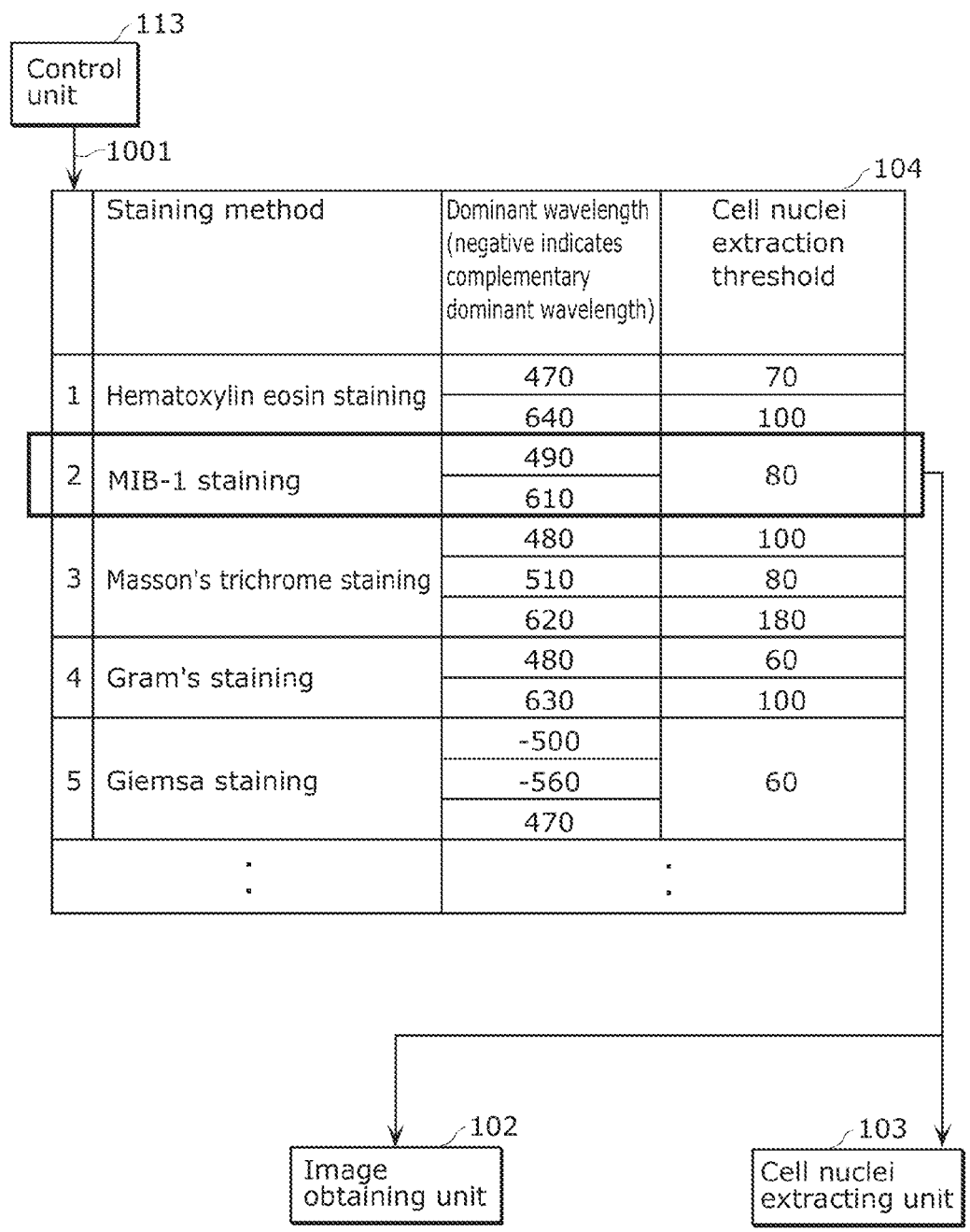
FIG. 12 is a diagram indicating an example of data stored in a threshold database unit.

Here, the threshold calculating unit 206 may store the positive cell nuclei extraction threshold in the threshold database unit 104 for each staining method as indicated in FIG. 12. Thus, the control unit 113 may control the image measurement apparatus 100 using an identification number 1001 of the staining method. Furthermore, the threshold calculating unit 206 stores the dominant wavelength of the positive cell nuclei, together with the positive cell nuclei extraction threshold. The operator may determine a positive cell nuclei extraction threshold from the distribution of the pixel values of the positive cell nuclei.

Furthermore, the threshold calculating unit 206 may calculate a threshold for extracting negative cell nuclei (hereinafter referred to as "negative cell nuclei extraction threshold") in the same manner as that of the positive cell nuclei extraction threshold, and store the threshold in the threshold database unit 104. Although in the example of FIG. 12, the positive cell nuclei extraction threshold is the same as the negative cell nuclei extraction threshold in the same staining method, they may be different.

When the threshold information is stored in the threshold database unit 104 in the preparation mode, the image measurement apparatus 100 changes from the preparation mode to the execution mode in accordance with the instruction from the control unit 113.

In the execution mode, the control unit 113 obtains the dominant wavelength of each color of the negative and positive cell nuclei from the threshold database unit 104 according to the staining method, and outputs the dominant wavelengths to the lighting unit 101. When the staining method is MIBI-1 staining in FIG. 12, the control unit 113 outputs, to the lighting unit 101, 610 nm as the dominant wavelength of the blown positive cell nuclei, and 490 nm as the dominant wavelength of the blue negative cell nuclei.

Figure 13:
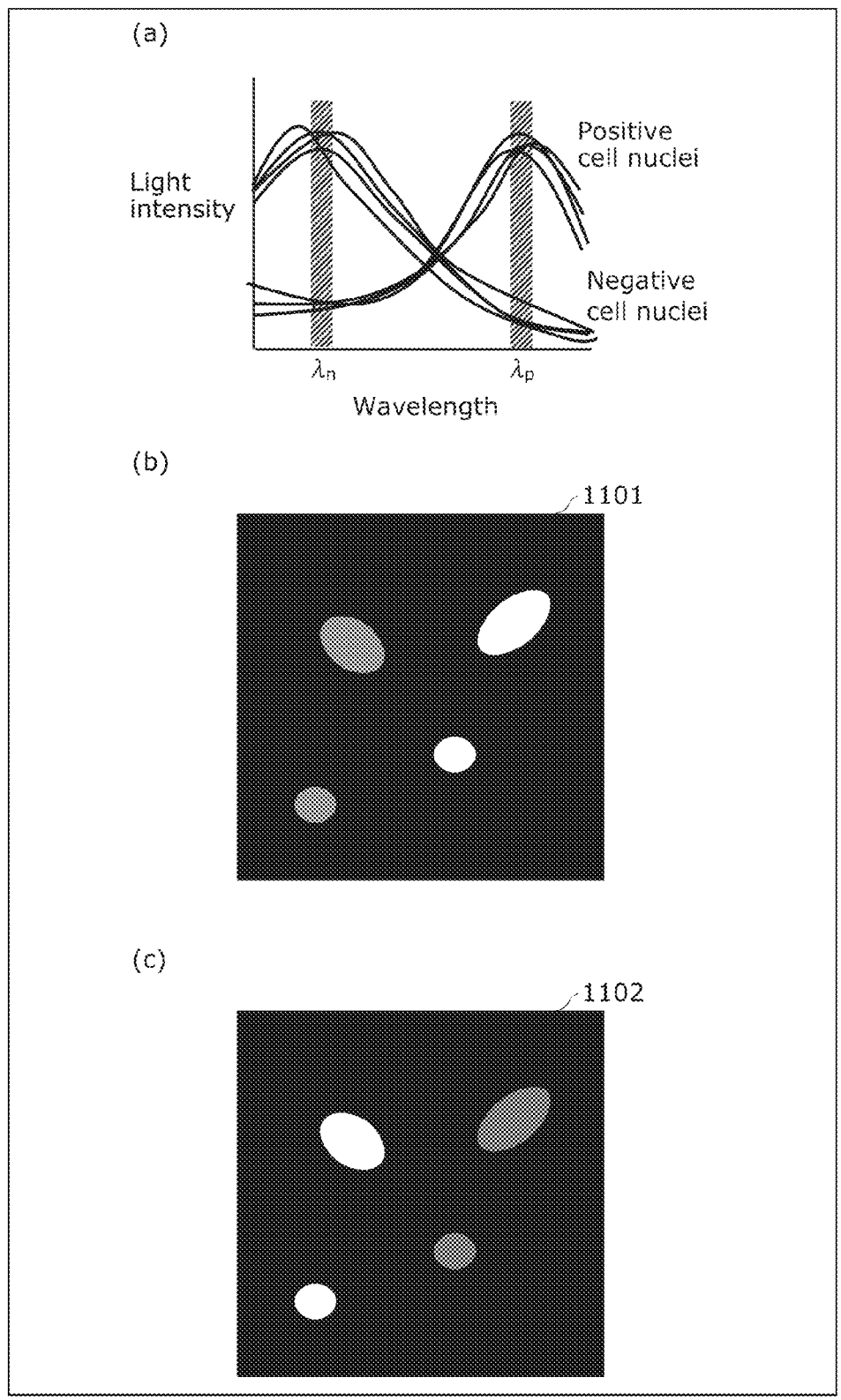
FIG. 13 illustrates an example of a dominant wavelength $\lambda_p$ reference image and a dominant wavelength $\lambda_n$ reference image.

When the negative and positive cell nuclei of the pathologic examination specimen 108 have the spectral distribution indicated in (a) of FIG. 13, the dominant wavelength $\lambda_p$ of the color of the positive cell nuclei is 610 nm and the dominant wavelength $\lambda_n$ of the color of the negative cell nuclei is 490 nm. A dominant-wavelength-$\lambda_p$ reference image 1101 indicated in (b) of FIG. 13 is an example of the examination image 111 obtained by emitting the narrowband light with the dominant wavelength $\lambda_p$ to the pathologic examination specimen 108.

A dominant-wavelength-$\lambda_n$ reference image 1102 indicated in (c) of FIG. 13 is an example of the examination image 111 obtained by emitting the narrowband light with the dominant wavelength $\lambda_n$ to the pathologic examination specimen 108. The thresholds for identifying the negative and positive cell nuclei are stored in the threshold database unit 104.

The cell nuclei extracting unit 103 extracts positive cell nuclei using a positive cell nuclei extraction threshold stored in the threshold database unit 104. In other words, the cell nuclei extracting unit 103 extracts pixels with pixel values larger than or equal to the positive cell nuclei extraction threshold from the dominant-wavelength-$\lambda_p$ reference image 1101, as the pixels of the positive cell nuclei. As will be described later, the total number of the cell nuclei is necessary to calculate the positive proportion. Thus, the cell nuclei extracting unit 103 extracts the negative cell nuclei in the same manner as the method of extracting the positive cell nuclei. In other words, the cell nuclei extracting unit 103 extracts pixels with pixel values larger than or equal to the negative cell nuclei extraction threshold from the dominant-wavelength-$\lambda_n$ reference image 1102 as the pixels of the negative cell nuclei. The sum of the positive and negative cell nuclei is the cell nuclei.

When the total number of cell nuclei or the total number of pixels of cell nuclei that is the sum of the negative and positive cell nuclei after removing pixels of cytoplasm that is a background image is known, it is not necessary to extract the negative cell nuclei. The cytoplasm area can be removed from the examination image 111 using a known technique. For example, the cytoplasm is higher in brightness and chroma than the cell nuclei. Thus, the cytoplasm area can be identified and removed from the examination image 111, by binarizing the examination image 111 using brightness and chroma. Here, the examination image 111 to be used for removing the cytoplasm is an image captured in a state where the light output from the light source 106 is directly emitted to the pathologic examination specimen 108 without passing through the narrowband light conversion unit 107.

The positive proportion calculating unit 105 calculates a positive proportion by dividing the number of pixels of the positive cell nuclei by a sum of pixels of the negative and positive cell nuclei. Equation 5 below expresses the positive proportion.

Positive proportion=the number of pixels of the positive cell nuclei/(the number of pixels of positive cell nuclei+the number of pixels of negative cell nuclei) (Equation 5)

The output unit 114 outputs the positive proportion calculated by the positive proportion calculating unit 105. For example, the output unit 114 may display the positive proportion on a screen of the display or store the positive proportion in a recording medium. Furthermore, the output unit 114 may transmit the positive proportion to other devices through a network.

The output of the narrowband light from the lighting unit 101 reduces blurring (out of focus) caused by the chromatic aberration in the imaging optical system, making the examination image 111 and the dominant wavelength reference image 301 clear images that are in focus.

Figure 14:
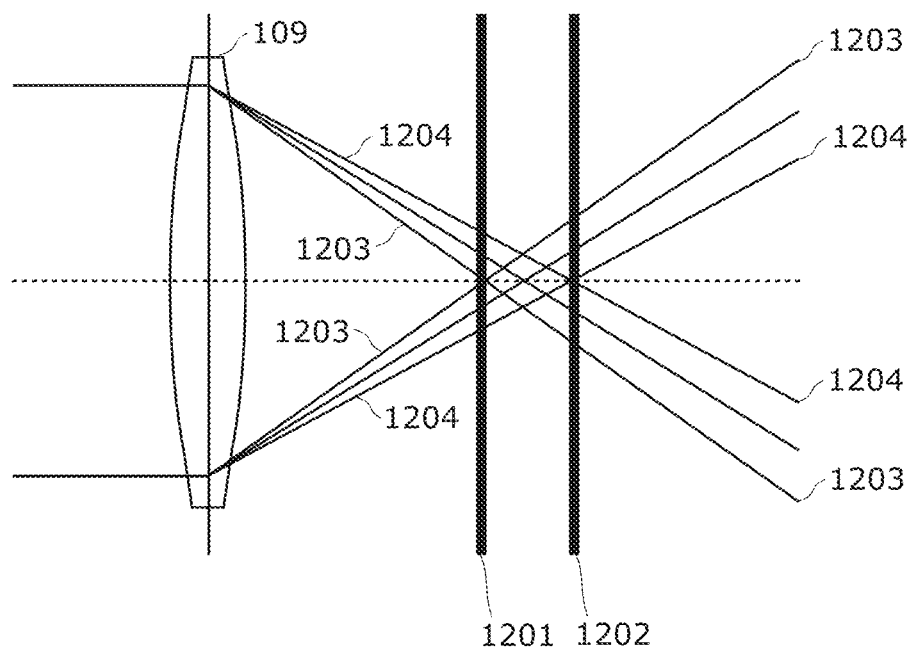
FIG. 14 illustrates a relationship between chromatic aberration and focus.

In other words, when the lighting unit 101 emits a blue light 1203 with a short wavelength as illustrated in FIG. 14, as long as the imaging sensor 110 is placed in a position 1201, only the focused light enters the imaging sensor 110 and the out-of-focus light does not enter the imaging sensor 110. Furthermore, when the lighting unit 101 emits a red light 1204 with a long wavelength, as long as the imaging sensor 110 is placed in a position 1202, only the focused light enters the imaging sensor 110 and the out-of-focus light does not enter the imaging sensor 110.

Since the blurring blurs the form of tissue, such as cell nuclei and cytoplasm, it adversely affects the calculation of positive proportions. However, changing the position of the imaging sensor 110 according to the wavelength of light emitted from the lighting unit 101 can suppress the influence of blurring. The control unit 113 controls the imaging sensor 110 for its position with the instruction.

When the light over the total visible light bandwidth enters the imaging sensor 110 to calculate the dominant wavelength as illustrated in FIG. 3, the reference image 201 has blurring. However, a colorimetric value for each pixel, that is, chromaticity coordinates are obtained for the reference image 201. Thus, the presence or absence of blurring does not affect the chromaticity coordinates. In other words, the presence or absence of blurring does not affect the calculation of a dominant wavelength.

According to Embodiment 1, it is possible to offset a color difference in pathological specimens occurring due to a difference in preparing specimens, and stably extract a specific target, such as negative and positive cell nuclei using a fixed threshold. Accordingly, the positive proportion can be calculated with high accuracy. Presentation of quantitative information obtained through image measurement to physicians or technicians enables the objective evidence to be added to the diagnosis criterion. Furthermore, emission of a narrowband light results in focused and clearer images.

Embodiment 2

Embodiment 2 describes an image measurement apparatus that can offset a color difference occurring due to a difference in preparing specimens and calculate a positive proportion using a fixed threshold database. Particularly, Embodiment 2 describes a method of calculating a dominant wavelength for each of tissues and increasing accuracy for extracting positive cell nuclei.

Figure 15:
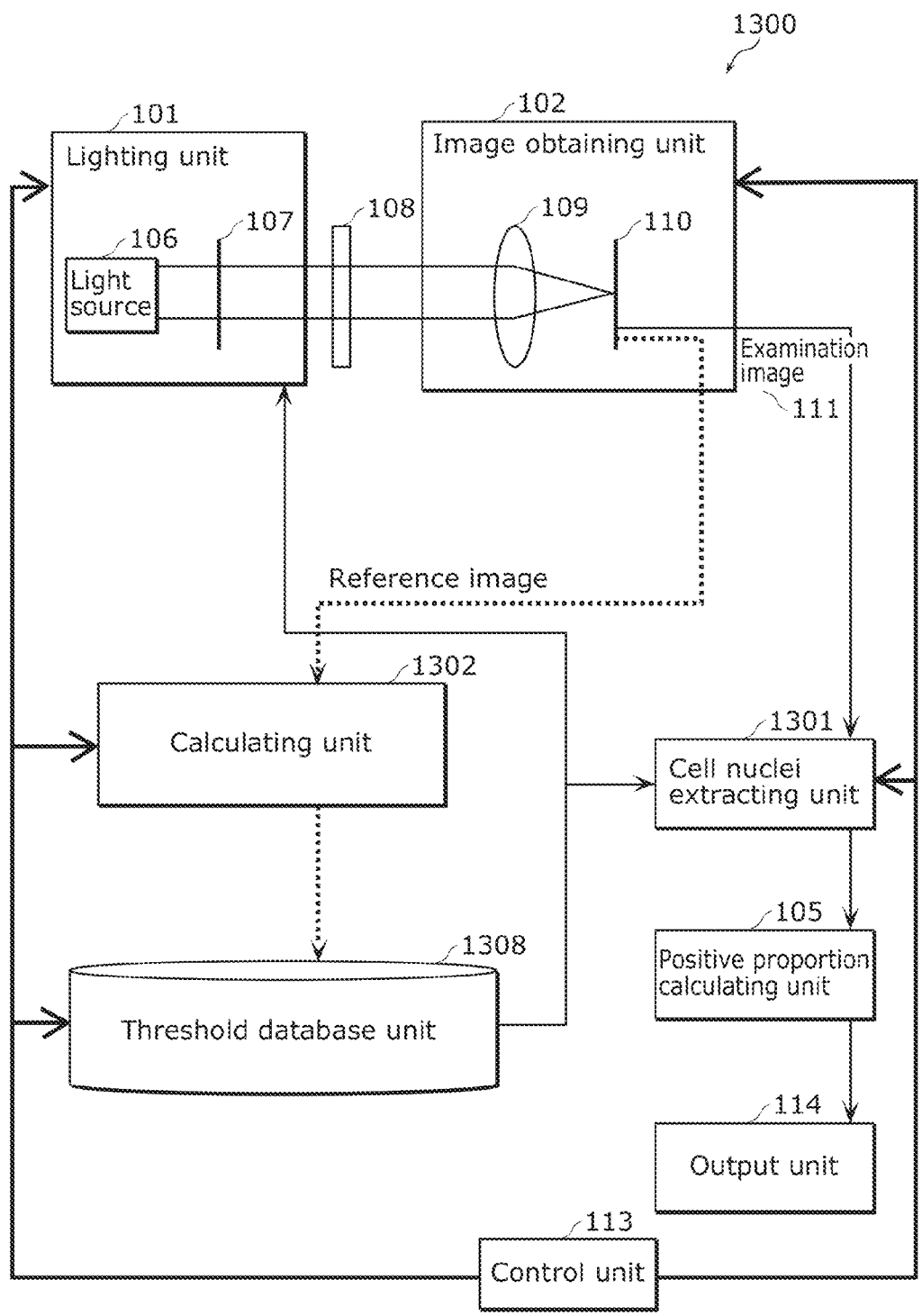
FIG. 15 is a block diagram illustrating a configuration of an image measurement apparatus according to Embodiment 2.

FIG. 15 is a block diagram illustrating a configuration of an image measurement apparatus 1300 according to Embodiment 2. The constituent elements identical to those in FIG. 1 are assigned to the same reference numerals, and thus the detailed description is not repeated. The image measurement apparatus 1300 includes a lighting unit 101, an image obtaining unit 102, a cell nuclei extracting unit 1301, a threshold database unit 1308, a positive proportion calculating unit 105, a calculating unit 1302, a control unit 113, and an output unit 114. The image measurement apparatus 1300 detects a positive proportion given from a pathologic examination specimen 108.

The cell nuclei extracting unit 1301 extracts positive cell nuclei from an examination image 111 that is captured by emitting a narrowband light including the dominant wavelengths other than the dominant wavelength of the positive cell nuclei to the pathologic examination specimen 108. The reason why the dominant wavelengths other than the dominant wavelength of the positive cell nuclei are used is to avoid a case where the positive cell nuclei and other tissues cannot be identified without differences in light intensity in-between.

Figure 16:
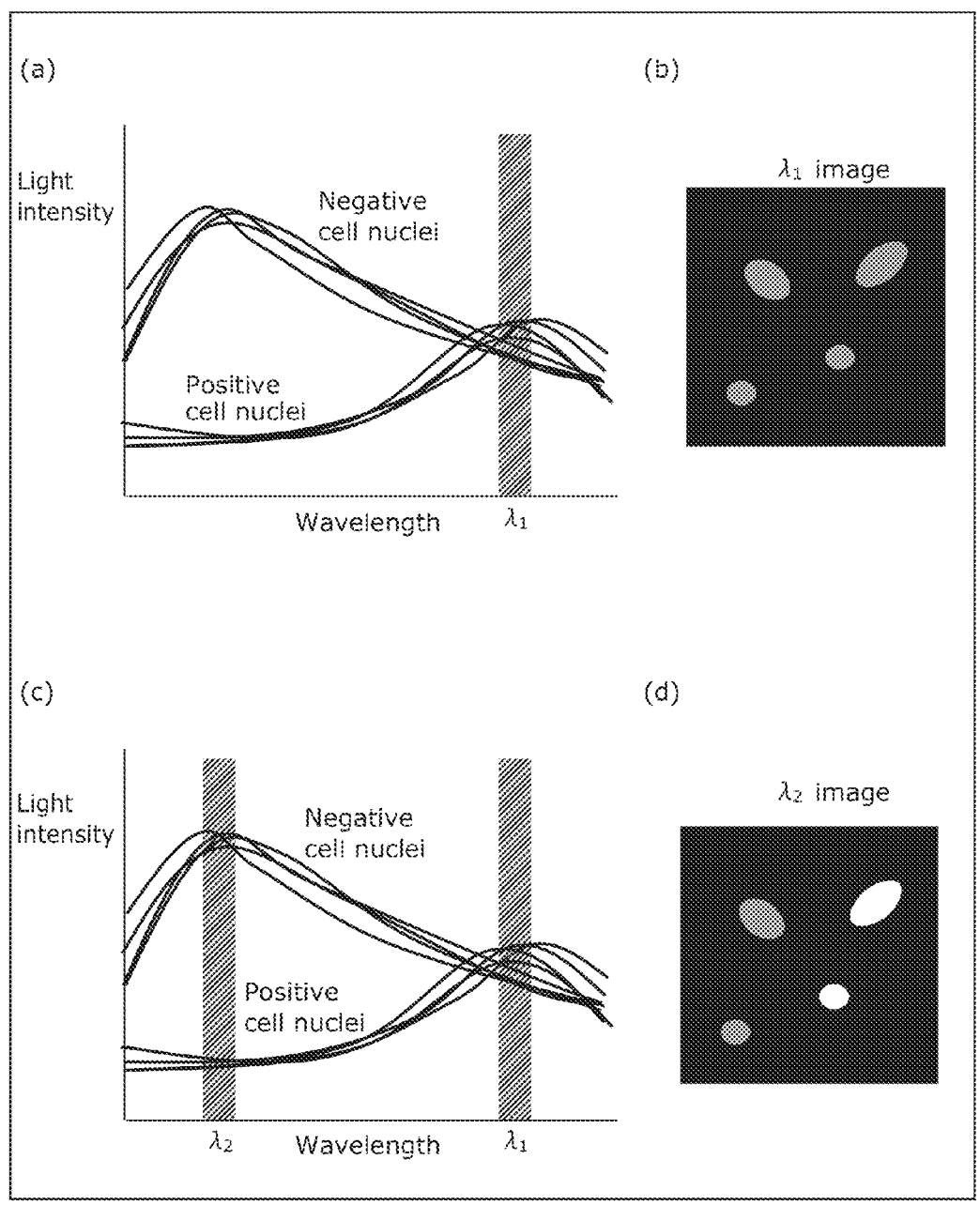
FIG. 16 illustrates an example of dominant wavelengths of negative and positive cell nuclei, and images obtained by emitting a narrowband light including the dominant wavelengths.

(a) of FIG. 16 is a graph indicating spectral distributions of negative and positive cell nuclei in tissue. Furthermore, (b) of FIG. 16 is an image when a narrowband light including the dominant wavelength $\lambda_1$ of the positive cell nuclei enters the tissue. As indicated in (a) and (b) of FIG. 16, there is no difference between light intensities of the negative and positive cell nuclei at the dominant wavelength $\lambda_1$ of the positive cell nuclei, and the negative and positive cell nuclei cannot be identified.

Thus, as indicated in (c) of FIG. 16 according to Embodiment 2, a dominant wavelength $\lambda_2$ of negative cell nuclei is also calculated aside from the dominant wavelength $\lambda_1$ of the positive cell nuclei to be extracted, to produce an image of the dominant wavelength $\lambda_2$ as indicated in (d) of FIG. 16.

The calculating unit 1302 calculates dominant wavelengths for each of pathological tissues included in a pathologic reference specimen in the preparation mode, and captures several dominant wavelength reference images. The pathological tissues are cell nuclei, cytoplasm, and others, and negative and positive cell nuclei segmented by the staining also belong to the pathological tissues.

Figure 17:
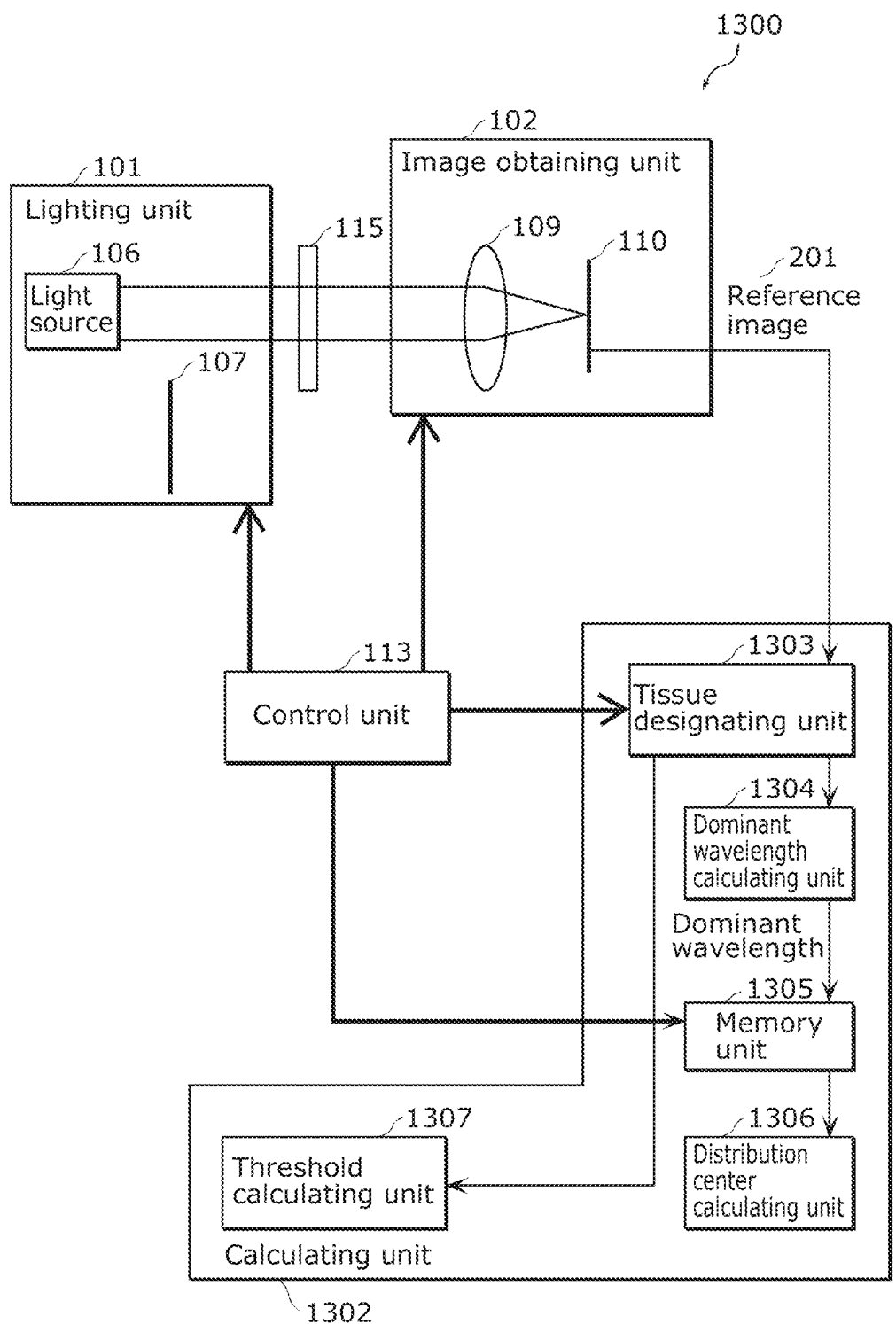
FIG. 17 illustrates calculation of a positive cell nuclei extraction threshold by an image measurement apparatus in the preparation mode.

FIG. 17 illustrates the calculation of a positive cell nuclei extraction threshold by the image measurement apparatus 1300 in the preparation mode.

The calculating unit 1302 includes a tissue designating unit 1303, a dominant wavelength calculating unit 1304, a memory unit 1305, a distribution center calculating unit 1306, and a threshold calculating unit 1307.

The issue designating unit 1303 designates the position of tissue from the reference image 201 of the pathologic reference specimen 115 to which the light over the total visible light bandwidth is emitted. For example, the tissue designating unit 1303 may cause the operator of the image measurement apparatus 1300 to designate the position of the tissue. Generally, the tissues have multiple categories. Thus, as illustrated FIG. 9, the operator designates the corresponding tissue by selecting the category of tissue using the cursor on the image.

The dominant wavelength calculating unit 1304 calculates a dominant wavelength for each category of the tissues. For example, the dominant wavelength calculating unit 1304 calculates a dominant wavelength for each of the negative and positive cell nuclei. The method of calculating the dominant wavelength is the same as that of calculating the dominant wavelength by the dominant wavelength calculating unit 203 according to Embodiment 1.

The memory unit 1305 holds dominant wavelengths for each category of the tissues.

The distribution center calculating unit 1306 calculates a distribution center of a dominant wavelength for each category of the tissues. The method of calculating the distribution center is the same as that of calculating the distribution center by the distribution center calculating unit 205 according to Embodiment 1.

Figure 18:
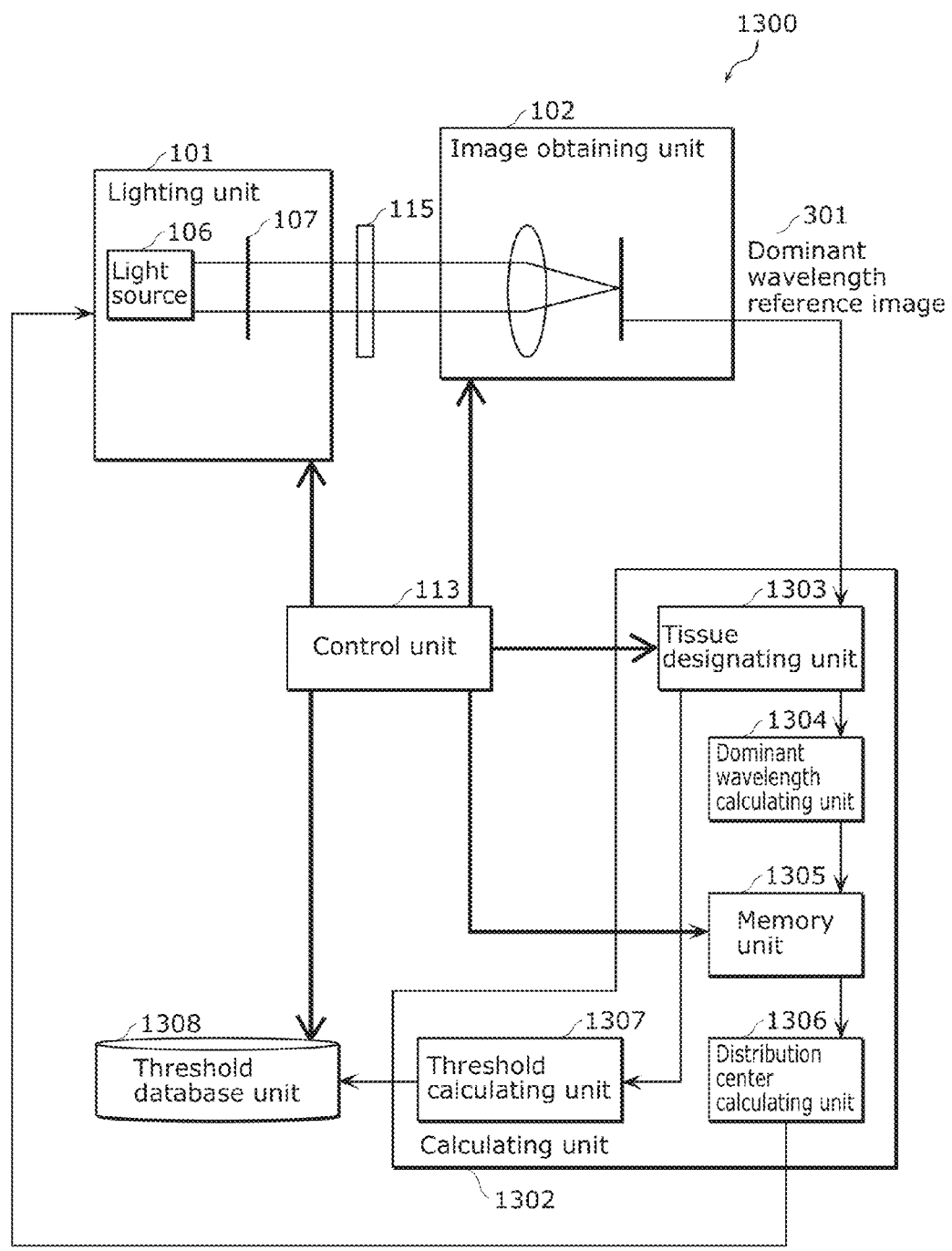
FIG. 18 illustrates processing of, for each tissue in the preparation mode, emitting a narrowband light including the dominant wavelength of the tissue to a pathologic reference specimen, and calculating a positive cell nuclei extraction threshold.

FIG. 18 illustrates processing of, for each of the tissues, emitting the narrowband light including the dominant wavelength of the tissues to the pathologic reference specimen 115 in the preparation mode, and calculating the positive cell nuclei extraction threshold.

The lighting unit 101 obtains the dominant wavelength for each of the tissues from the distribution center calculating unit 1306, and emits the narrowband light having the dominant wavelength as the center wavelength to the pathologic reference specimen 115. The distribution center calculating unit 1306 provides dominant wavelengths. Thus, the image obtaining unit 102 captures a dominant wavelength reference image 301 for each of the dominant wavelengths corresponding to the categories of the tissues.

The threshold calculating unit 1307 checks the distribution of pixel values for each of the types of tissues included in the dominant wavelength reference image 301, and calculates the threshold for extracting the tissues.

Figure 19:
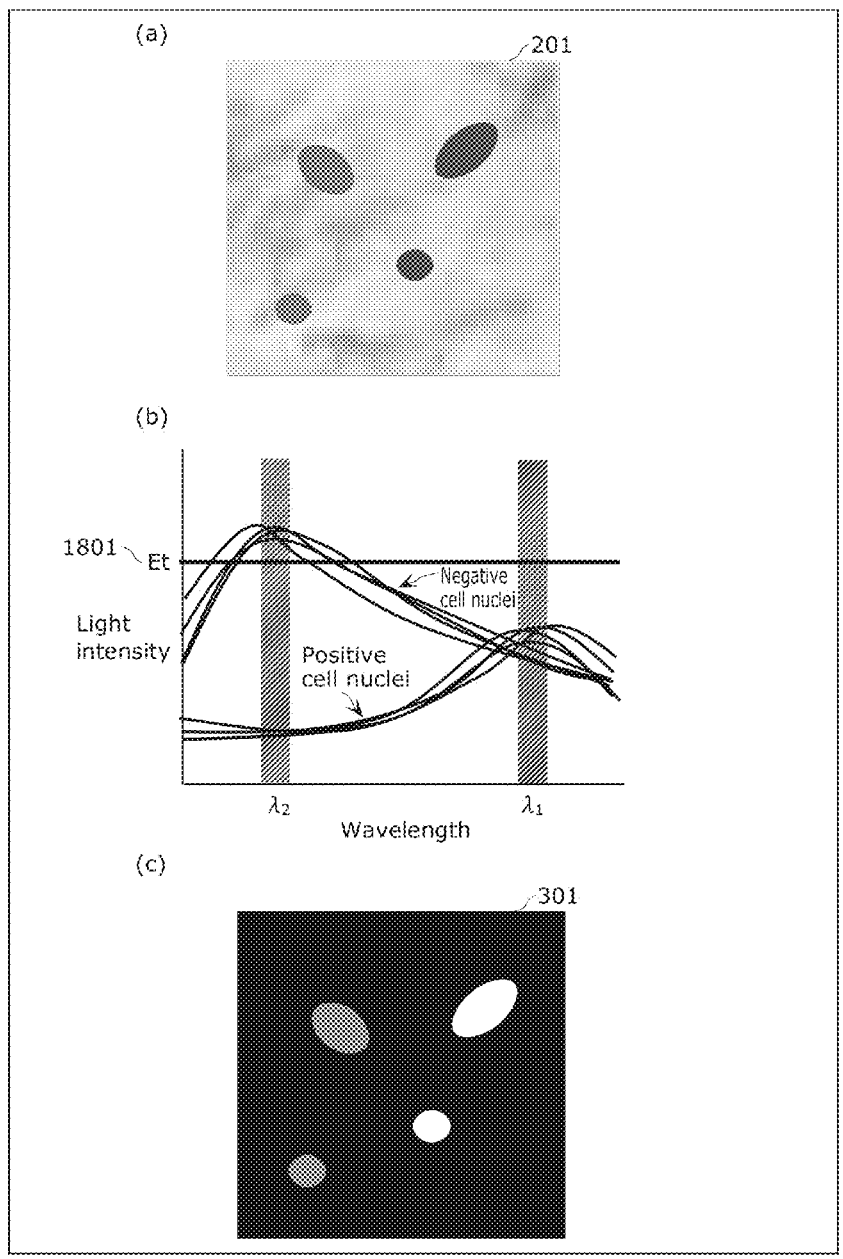
FIG. 19 illustrates an example of a method of setting a threshold for extracting positive cell nuclei.

In a reference image 201 of (a) of FIG. 19, suppose that the spectral distributions of the negative and positive cell nuclei are defined as in (b) of FIG. 19. Here, (c) of FIG. 19 shows the dominant wavelength reference image 301 corresponding to the dominant wavelength $\lambda_2$ of the negative cell nuclei. Thus, it is possible to determine that the pixels with the pixel values smaller than that of a light intensity Et1801 are pixels of the positive cell nuclei, at the dominant wavelength $\lambda_2$ of the negative cell nuclei.

Here, the pixels of the cytoplasm corresponding to the background image are removed from the dominant wavelength reference image 301. The method of removing the pixels of the cytoplasm is as described in Embodiment 1. The threshold calculating unit 1307 stores the calculated thresholds for extracting each of tissues, in the threshold database unit 1308.

After completion of storing the threshold information in the threshold database unit 1308 in the preparation mode, the image measurement apparatus 1300 changes from the preparation mode to the execution mode in accordance with the instruction from the control unit 113.

In the execution mode, the control unit 113 obtains the dominant wavelength from the threshold database unit 1308 according to the staining method, and provides the wavelength to the lighting unit 101. In the example of FIG. 16, the control unit 113 provides the wavelength $\lambda_2$ as the dominant wavelength to the lighting unit 101. The lighting unit 101 sets the wavelength of the narrowband light conversion unit 107 to the wavelength $\lambda_2$.

The cell nuclei extracting unit 1301 obtains a threshold for identifying each of the tissues from the threshold database unit 1308, and extracts the positive cell nuclei by binarizing the examination image 111 using the threshold.

According to Embodiment 2, it is possible to offset a color difference in pathological specimens occurring due to a difference in preparing specimens, and stably extract a specific target, such as negative and positive cell nuclei using a fixed threshold. Accordingly, the positive proportion can be calculated with high accuracy. Presentation of quantitative information obtained through image measurement to physicians or technicians enables the objective evidence to be added to the diagnosis criterion. Furthermore, emission of a narrowband light results in focused and clearer images.

Embodiment 3

Embodiment 3 describes an image measurement apparatus that can offset a color difference occurring due to a difference in preparing specimens and calculate a positive proportion using a fixed threshold database. Particularly, Embodiment 3 describes, when the dominant wavelength of the color of positive cell nuclei cannot be uniquely determined, a method of calculating a dominant wavelength of a complementary color (complementary dominant wavelength) of the positive cell nuclei to extract the positive cell nuclei.

Figure 20:
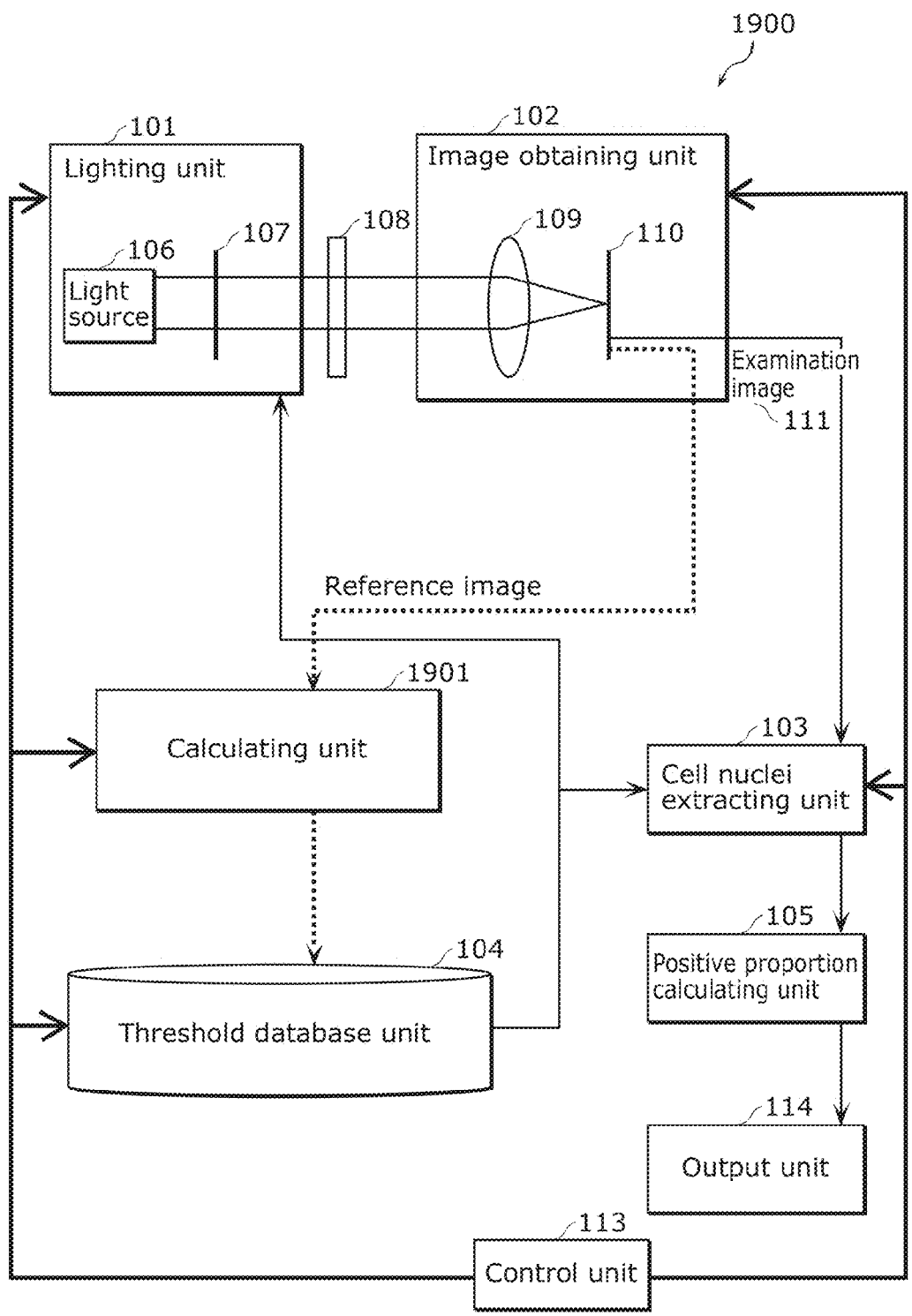
FIG. 20 is a block diagram illustrating a configuration of an image measurement apparatus according to Embodiment 3.

FIG. 20 is a block diagram illustrating a configuration of an image measurement apparatus 1900 according to Embodiment 3. The constituent elements identical to those in FIG. 1 are assigned to the same reference numerals, and thus the detailed description is not repeated. The image measurement apparatus 1900 includes a lighting unit 101, an image obtaining unit 102, a cell nuclei extracting unit 103, a threshold database unit 104, a positive proportion calculating unit 105, a calculating unit 1901, and a control unit 113.

When the dominant wavelength of the color of the positive cell nuclei cannot be uniquely determined in the preparation mode, the calculating unit 1901 calculates a positive cell nuclei extraction threshold using, as a processing target, a reference image of the pathologic reference specimen to which the narrowband light including the complementary dominant wavelength of the positive cell nuclei is emitted.

Figure 21:
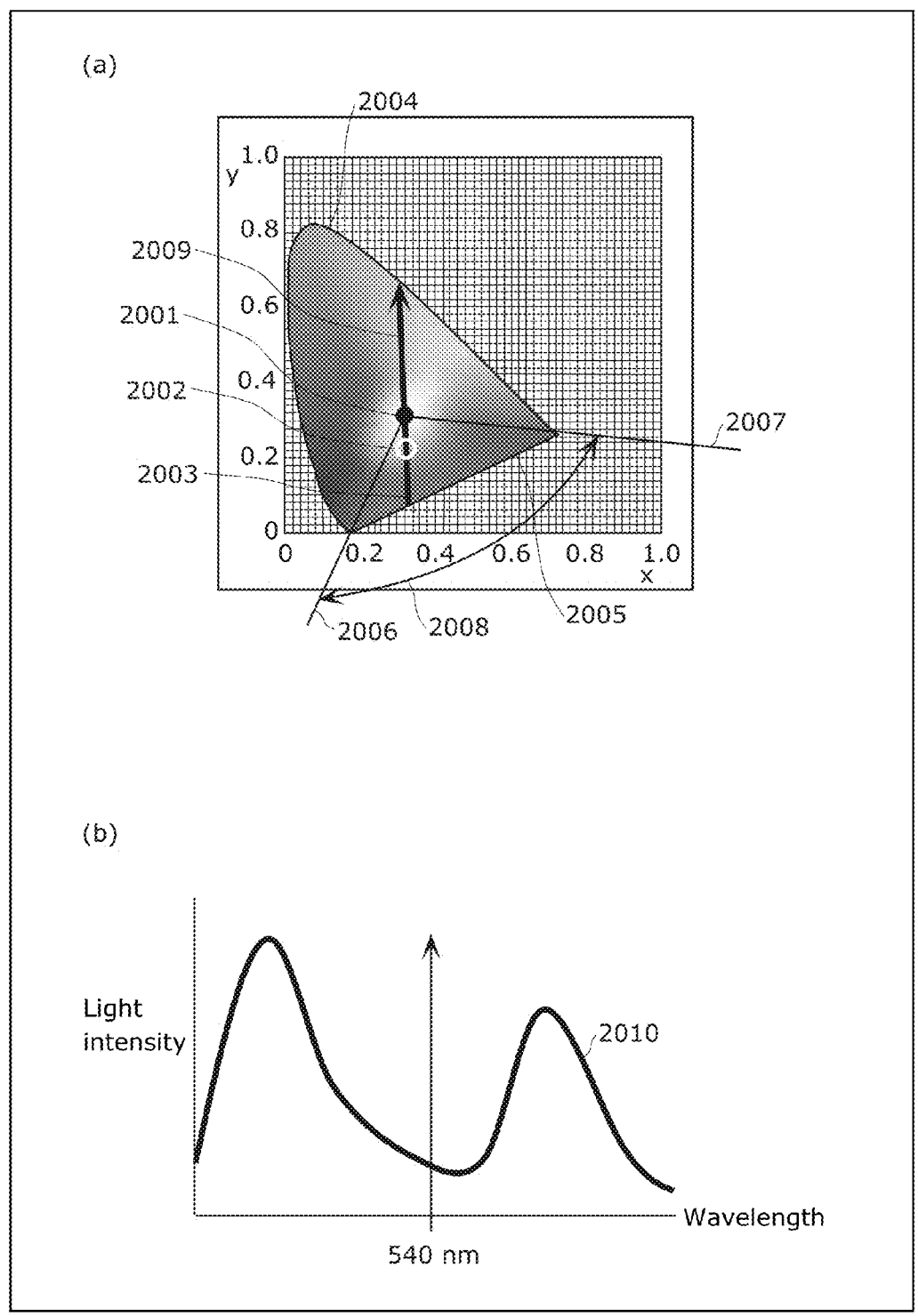
FIG. 21 illustrates a complementary dominant wavelength.

When a line 2003 extending from a white point 2001 to a target color point 2002 crosses not a spectral locus 2004 but a red-purple line 2005 as illustrated in (a) of FIG. 21, the dominant wavelength of the target color cannot be calculated. The red-purple line 2005 is a line connecting blue with a shortest wavelength (380 nm) to red with a longest wavelength (780 nm). The colors without any dominant wavelength exist in an area 2008 between a line 2006 and a line 2007, and these colors have approximately two crests as a spectral distribution 2010 indicated in (b) of FIG. 21.

The complementary dominant wavelength is a wavelength in which a line 2009 crosses the spectral locus 2004.

The line 2009 is obtained by extending the line 2003 from the white point 2001 to the target color point 2002, in an opposite hue direction. In the example of (a) of FIG. 21, the complementary dominant wavelength is 540 nm, and corresponds to a wavelength with a low light intensity in the spectral distribution 2010 in (b) of FIG. 21.

Figure 22:
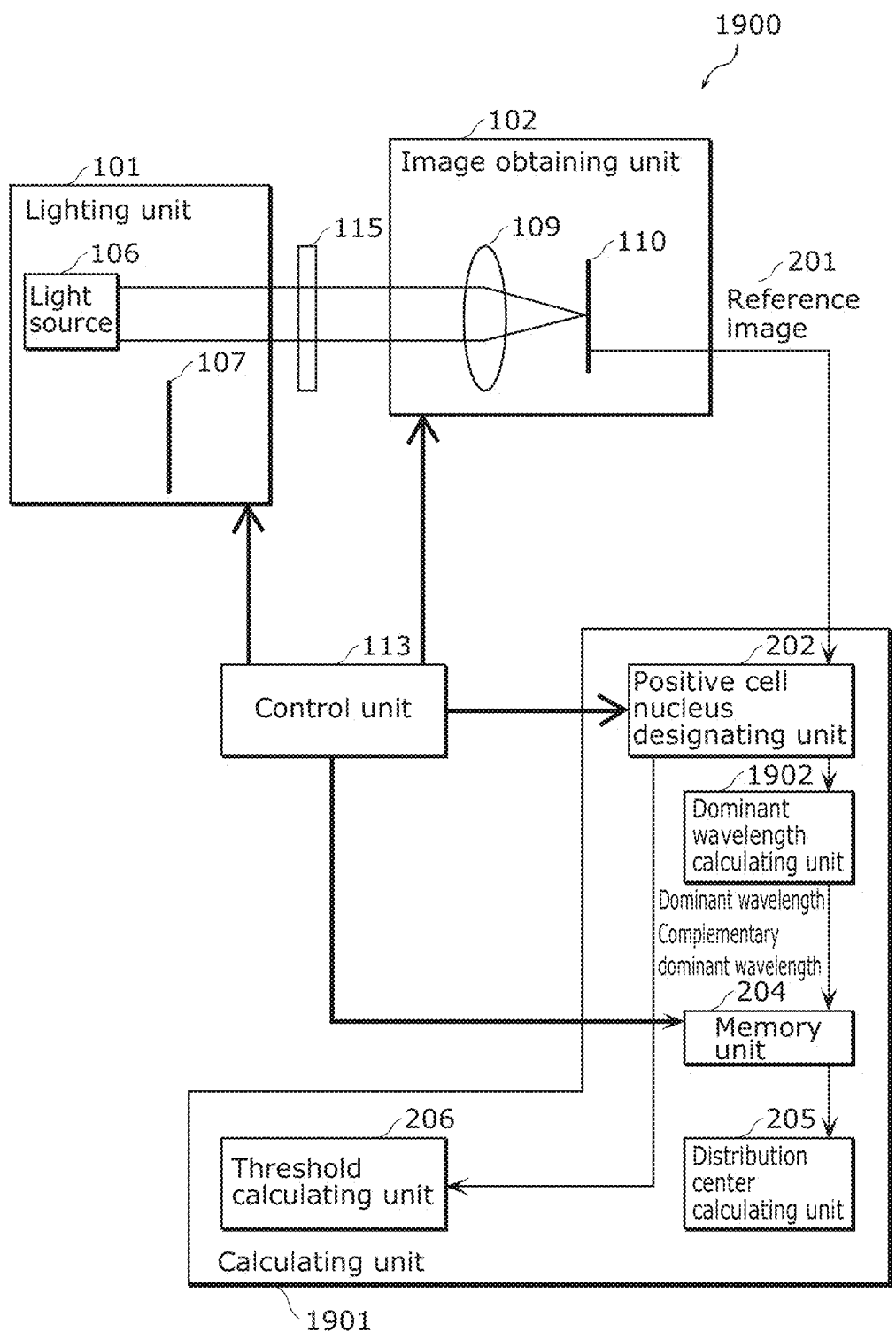
FIG. 22 illustrates calculation of a positive cell nuclei extraction threshold by an image measurement apparatus in the preparation mode.

FIG. 22 illustrates the calculation of a positive cell nuclei extraction threshold by the image measurement apparatus 1900 in the preparation mode.

The calculating unit 1901 includes a positive cell nucleus designating unit 202, a dominant wavelength calculating unit 1902, a memory unit 204, a distribution center calculating unit 205, and a threshold calculating unit 206.

The dominant wavelength calculating unit 1902 calculates a complementary dominant wavelength when the dominant wavelength of the color of the positive cell nuclei cannot be obtained. In other words, the dominant wavelength calculating unit 1902 calculates a complementary dominant wavelength for the colors in the area 2008 of (a) of FIG. 21. Furthermore, the dominant wavelength calculating unit 1902 calculates a dominant wavelength for the colors in an area other than the area 2008.

In the execution mode, when the positive cell nuclei extraction threshold for the dominant wavelength of the color of positive cell nuclei is used, the cell nuclei extracting unit 103 determines a pixel having a pixel value larger than the threshold as a pixel of a positive cell nucleus. When the positive cell nuclei extraction threshold for the complementary dominant wavelength of colors of positive cell nuclei is used, the cell nuclei extracting unit 103 determines a pixel having a pixel value smaller than the threshold as a pixel of a positive cell nucleus.

According to Embodiment 3, it is possible to offset a color difference in pathological specimens occurring due to a difference in preparing specimens, and identify negative and positive cell nuclei using a fixed threshold when the negative or positive cell nuclei have a complementary dominant wavelength. Accordingly, the positive proportion can be calculated with high accuracy. Presentation of quantitative information obtained through image measurement to physicians or technicians enables the objective evidence to be added to the diagnosis criterion. Furthermore, emission of a narrowband light results in focused and clearer images.

INDUSTRIAL APPLICABILITY

The image measurement apparatus and method according to one or more exemplary embodiments disclosed herein can offset a color difference occurring due to a difference in preparing specimens, and efficiently and objectively identify a specific target, such as negative and positive cell nuclei and cytoplasm. Furthermore, the positive proportion can be calculated with high accuracy. Thus, one or more exemplary embodiments of the present disclosure are applicable to image measurement apparatuses and others that calculate positive proportions from the pathologic examination specimens.

The invention claimed is:
1. An image measurement apparatus, comprising:
a lighting unit configured to emit a first narrowband light that is a light with a bandwidth (i) narrower than a bandwidth of a visible light and (ii) including a dominant wavelength of a color of a positive cell nucleus, and configured to emit a broadband light that is a light with a bandwidth broader than the bandwidth of the first narrowband light;
an image obtaining unit configured to obtain an examination image by capturing an image of a pathologic examination specimen to which the first narrowband light is emitted, and configured to obtain a reference image by capturing an image of a pathologic reference specimen to which the broadband light is emitted;
a dominant wavelength calculating unit configured to calculate the dominant wavelength of the color of the positive cell nucleus included in the reference image;
a threshold calculating unit configured to calculate, as a predetermined threshold, a threshold for extracting pixels of positive cell nuclei from the reference image by performing threshold processing, based on a light intensity of the dominant wavelength calculated by the dominant wavelength calculating unit;
a cell nuclei extracting unit configured to extract pixels of positive cell nuclei from the examination image by comparing pixel values of the examination image with the predetermined threshold;
a positive proportion calculating unit configured to calculate a proportion of the positive cell nuclei among cell nuclei included in the pathologic examination specimen, using the pixels of the positive cell nuclei extracted by the cell nuclei extracting unit; and
an output unit configured to output the proportion calculated by the positive proportion calculating unit.

2. The image measurement apparatus according to claim 1,
wherein the dominant wavelength calculating unit is configured to calculate a dominant wavelength of each of colors of the positive cell nuclei included in the reference image, the colors of the positive cell nuclei including the color of the positive cell nucleus,
the image measurement apparatus further comprises a distribution center calculating unit configured to calculate a center wavelength of the dominant wavelengths of the colors of the positive cell nuclei calculated by the dominant wavelength calculating unit, and
the lighting unit is configured to emit, as the first narrowband light, a light with a bandwidth (i) narrower than the bandwidth of the visible light and (ii) including the center wavelength calculated by the distribution center calculating unit.

3. The image measurement apparatus according to claim 1,
wherein the dominant wavelength calculating unit is further configured to calculate a complementary dominant wavelength of colors of the positive cell nuclei included in the reference image when the colors do not have any dominant wavelength,
the threshold calculating unit is configured to calculate, as the predetermined threshold, a threshold for extracting pixels of the positive cell nuclei from the reference image by performing the threshold processing, based on a light intensity of the complementary dominant wavelength calculated by the dominant wavelength calculating unit,
the lighting unit is configured to emit, in place of the first narrowband light, a second narrowband light that is a light with a bandwidth (i) narrower than the bandwidth of the visible light and (ii) including the complementary dominant wavelength, and
the image obtaining unit is further configured to obtain an examination image by capturing an image of a pathologic examination specimen to which the second narrowband light is emitted.

4. The image measurement apparatus according to claim 1,
wherein the lighting unit is configured to emit, in place of the first narrowband light, a third narrowband light that is a light with a bandwidth (i) narrower than the bandwidth of the visible light and (ii) including a dominant wavelength of a color of a tissue other than the positive cell nuclei, and
the image obtaining unit is further configured to obtain an examination image by capturing an image of a pathologic examination specimen to which the third narrowband light is emitted.

5. The image measurement apparatus according to claim 4,
wherein the dominant wavelength calculating unit is further configured to calculate the dominant wavelength of the color of the tissue included in the reference image, and
the threshold calculating unit is further configured to calculate, as the predetermined threshold, a threshold for extracting the pixels of the positive cell nuclei from the reference image by performing the threshold processing, based on a light intensity of the dominant wavelength of the color of the tissue calculated by the dominant wavelength calculating unit.

6. The image measurement apparatus according to claim 1, further comprising
a control unit configured to move an imaging surface of the image obtaining unit to a position on which the first narrowband light is focused, the first narrowband light being emitted by the lighting unit.

7. The image measurement apparatus according to claim 1,
wherein the bandwidth of the first narrowband light is smaller than a bandwidth of a light that passes through one of RGB color filters.

8. An image measurement method, comprising:
emitting a broadband light that is a light with a predetermined bandwidth;
obtaining a reference image by capturing an image of a pathologic reference specimen to which the broadband light is emitted;
calculating a dominant wavelength of a color of a positive cell nucleus included in the reference image;
calculating, as a predetermined threshold, a threshold for extracting pixels of positive cell nuclei from the reference image by performing threshold processing, based on a light intensity of the calculated dominant wavelength;
emitting a narrowband light that is a light with a bandwidth narrower than the bandwidth of the broadband light and including the dominant wavelength;
obtaining an examination image by capturing an image of a pathologic examination specimen to which the narrowband light is emitted;
extracting pixels of positive cell nuclei from the examination image by comparing pixel values of the examination image with the predetermined threshold;
calculating a proportion of the positive cell nuclei among cell nuclei included in the pathologic examination specimen using the extracted pixels of the positive cell nuclei; and
outputting the calculated proportion.

9. A non-transitory computer-readable recording medium on which a program causing a computer to execute the image measurement method according to claim 8 is recorded.

* * * * *